(12) United States Patent
Okamoto

(10) Patent No.: US 8,961,402 B2
(45) Date of Patent: Feb. 24, 2015

(54) ENDOSCOPE

(71) Applicant: Olympus Medical Systems Corp., Tokyo (JP)

(72) Inventor: Yasuhiro Okamoto, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/923,423

(22) Filed: Jun. 21, 2013

(65) Prior Publication Data

US 2013/0338441 A1    Dec. 19, 2013

Related U.S. Application Data

(63) Continuation of application No. PCT/JP2013/050142, filed on Jan. 9, 2013.

(30) Foreign Application Priority Data

Jan. 16, 2012   (JP) .................................. 2012-006303

(51) Int. Cl.
   *A61B 1/00*        (2006.01)
   *A61B 1/005*      (2006.01)
   *A61B 1/04*        (2006.01)

(52) U.S. Cl.
   CPC .................................. *A61B 1/0052* (2013.01)
   USPC ........................................ 600/146; 600/139

(58) Field of Classification Search
   CPC ..... A61B 1/005; A61B 1/0051; A61B 1/0057
   USPC ................. 600/139, 146, 148, 149, 140–145; 348/45; 356/241.1
   See application file for complete search history.

(56) References Cited

U.S. PATENT DOCUMENTS

| | | | |
|---|---|---|---|
| 4,986,257 A | | 1/1991 | Chikama |
| 2003/0092965 A1 | * | 5/2003 | Konomura et al. ........... 600/146 |
| 2004/0193014 A1 | * | 9/2004 | Miyagi et al. .................. 600/146 |
| 2008/0207998 A1 | * | 8/2008 | Maruyama ..................... 600/114 |

FOREIGN PATENT DOCUMENTS

| | | |
|---|---|---|
| EP | 0 415 553 A1 | 7/1990 |
| JP | 56-56302 U | 5/1981 |
| JP | 3-60625 A | 3/1991 |
| JP | 2000-126119 A | 5/2000 |
| JP | 2003-325437 A | 11/2003 |
| JP | 2004-321492 A | 11/2004 |
| JP | 2009-101076 A | 5/2009 |

\* cited by examiner

*Primary Examiner* — Anhtuan T Nguyen
*Assistant Examiner* — Timothy J Neal
(74) *Attorney, Agent, or Firm* — Scully, Scott, Murphy & Presser, PC

(57) ABSTRACT

An endoscope includes an insertion portion, a bending portion bendable in an up-down direction and a left-right direction, a traction member for bending the bending portion, an operation portion provided at a proximal end of the insertion portion, an operation input portion provided in the operation portion, tiltable with respect to a first direction for bending the bending portion in the up-down direction and a second direction for bending the bending portion in the left-right direction, and for performing an operation input for acting on the traction member according to tilting operation and bending the bending portion, and an operation force amount adjusting portion configured to adjust an operation force amount for tilting the operation input portion in the first direction and an operation force amount for tilting the operation input portion in the second direction to be different.

10 Claims, 16 Drawing Sheets

FIG.14
(A)
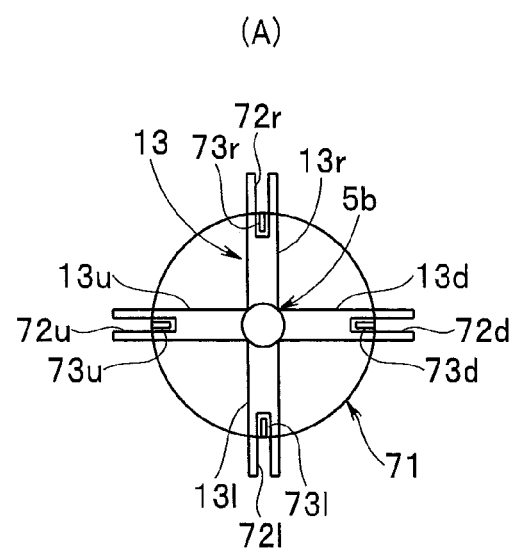
(B)
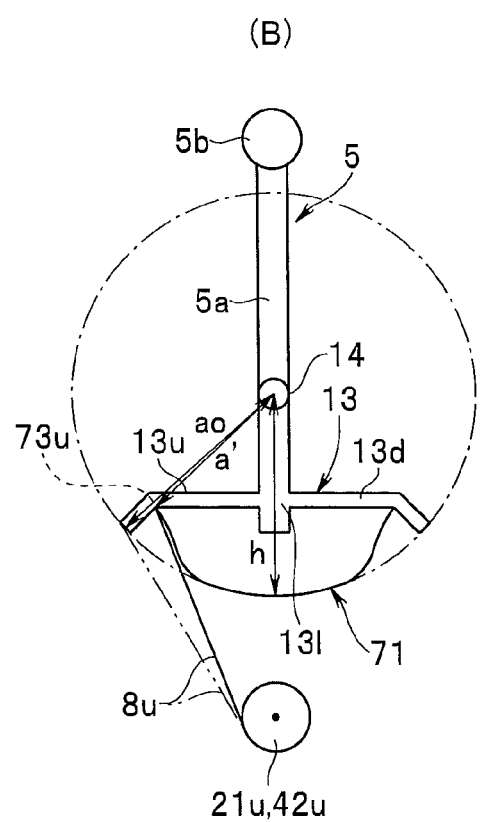

FIG.16
(A)
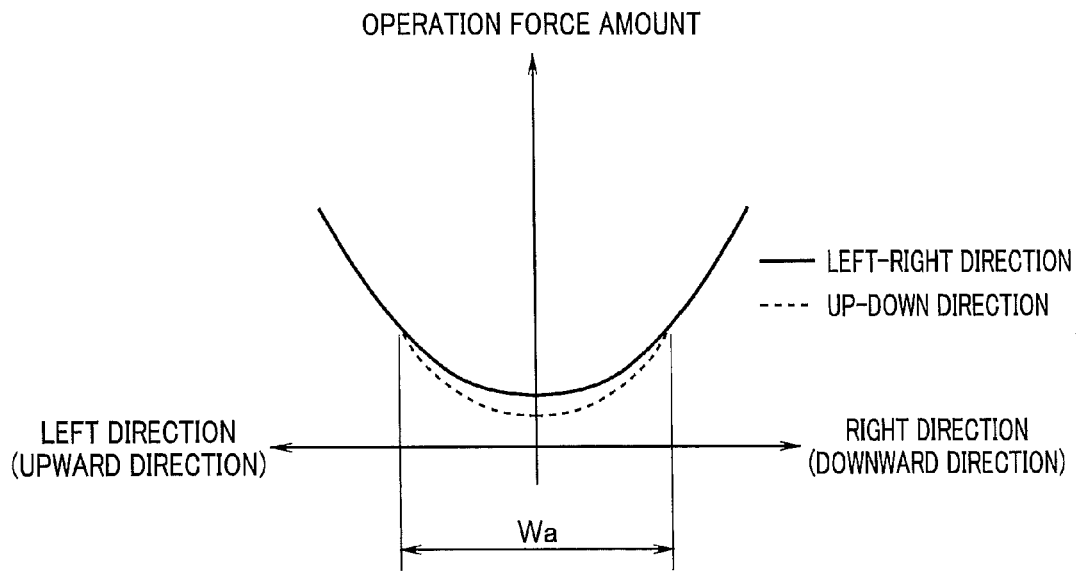
(B)
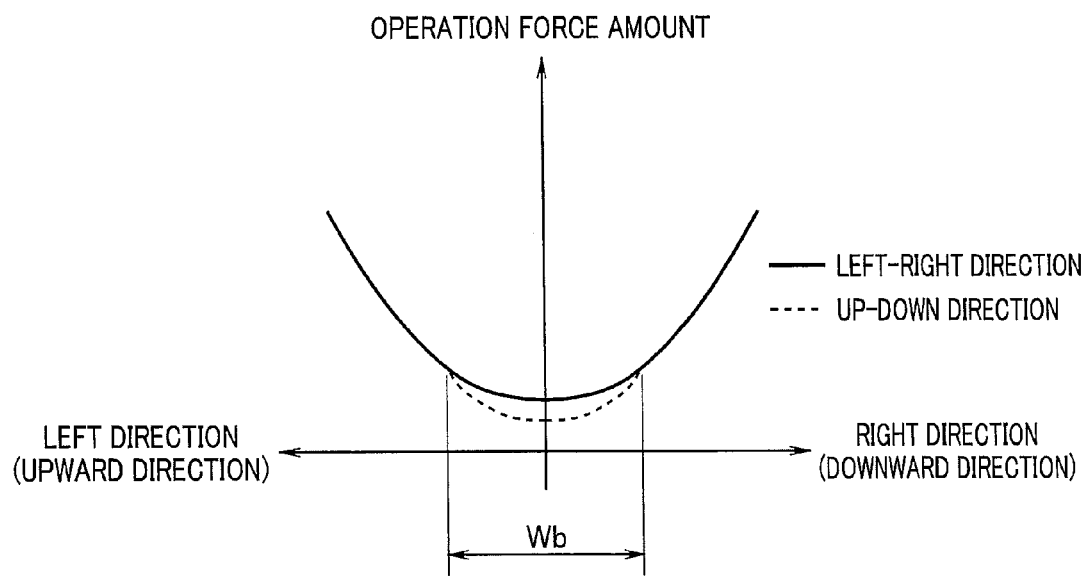

ENDOSCOPE

CROSS REFERENCE TO RELATED APPLICATION

This application is a continuation application of PCT/JP2013/050142 filed on Jan. 9, 2013 and claims benefit of Japanese Application No. 2012-006303 filed in Japan on Jan. 16, 2012, the entire contents of which are incorporated herein by this reference.

BACKGROUND OF THE INVENTION

1. Field of the Invention

The present invention relates to an endoscope in which a bending portion is driven to be bent.

2. Description of the Related Art

In recent years, an endoscope has been widely used in a medical field and an industrial field. A bendable bending portion is provided on a distal end side of an insertion portion in the endoscope to make it easy to insert the endoscope into even a bent region.

The bending portion is coupled to an operation input portion for bending provided on a proximal end side of the insertion portion via a bending operation wire functioning as a traction member inserted through the insertion portion. An operator can tow the bending operation wire and bend the bending portion by pivoting a bending knob configuring the operation input portion.

When the bending portion is driven to be bent manually by the operator, a large operation force amount is necessary. Therefore, there is proposed an endoscope of an electric assist system in which a traction member is towed via electric driving means by tilting operation of a manipulator such as an operation lever or a joystick configuring an operation input portion.

For example, Japanese Patent Application Laid-Open Publication No. 2003-325437 discloses that a strained state of a bending operation wire corresponding to tilting operation fixed to a coupling member is changed by tilting a manipulator, whereby a C-ring member that is pivotably arranged on the outer side of a pulley rotated by a motor and around which the bending operation wire is wound is reduced in diameter, a friction force is generated between the C-ring member reduced in diameter and the pulley, the C-ring member is rotated together with the pulley, and the bending operation wire is moved in a direction of the rotation, whereby a bending portion is bent.

In this way, in the case of the endoscope of the electric assist system, compared with the manual bending of the bending portion, it is possible to bend the bending portion with a small operation force amount by the tilting operation of the manipulator.

SUMMARY OF THE INVENTION

An endoscope according to an aspect of the present invention includes: an insertion portion; a bending portion provided in the insertion portion and bendable in an up-down direction and a left-right direction; a traction member for bending the bending portion; an operation portion provided at a proximal end of the insertion portion and for grasping by an operator; an operation input portion provided in the operation portion, tiltable with respect to a direction for bending the bending portion in the up-down direction and a direction for bending the bending portion in the left-right direction, and for performing an operation input for acting on the traction member according to tilting operation and bending the bending portion; and an operation force amount adjusting portion configured to adjust an operation force amount for tilting the operation input portion in the direction for bending the bending portion in the up-down direction and an operation force amount for tilting the operation input portion in the direction for bending the bending portion in the left-right direction to be different.

BRIEF DESCRIPTION OF THE DRAWINGS

FIG. 14 is a diagram showing a schematic configuration of a peripheral portion of a manipulator in a third modification of the first embodiment.

FIG. 16 is a characteristic chart showing a distribution of an operation force amount obtained when a manipulator is tilted in a left-right direction and an up-down direction in the second embodiment.

DETAILED DESCRIPTION OF THE PREFERRED EMBODIMENTS

Embodiments of the present invention are explained below with reference to the drawings.

First Embodiment

Figure 1:
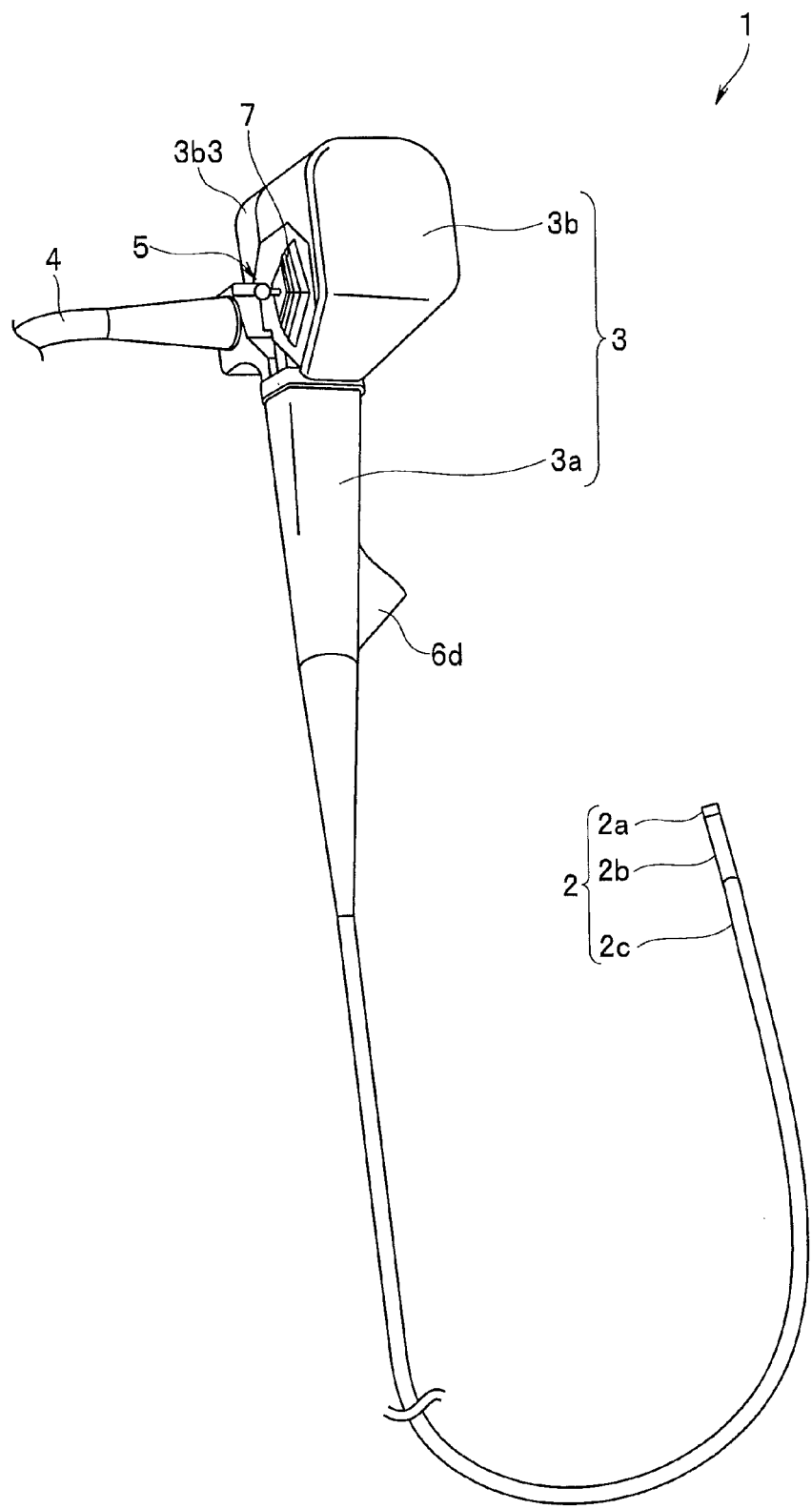
FIG. 1 is a perspective view showing an endoscope in a first embodiment of the present invention.

As shown in FIG. 1, an endoscope 1 of the present invention is an endoscope of an electric assist system. The endoscope 1 includes an elongated insertion portion 2, an operation portion 3 jointly provided to a proximal end of the insertion portion 2, and a universal cord 4 extending from a side portion of the operation portion 3.

The insertion portion 2 is formed by jointly providing, in order from a distal end side, a rigid distal end portion 2a, a bending portion 2b bendable in up-down and left-right directions, and a flexible tube portion 2c having flexibility and formed long. An illumination window and an observation widow are provided in the distal end portion 2a. Illumination light is emitted from the illumination window. A not-shown image pickup apparatus configured to pick up an image of an illuminated region is provided in the observation window.

The operation portion 3 includes a grasping portion 3a jointly provided to a proximal end (a rear end) of the insertion portion 2 and an operation portion main body 3b jointly provided to a proximal end of the grasping portion 3a. A longitudinal axis of the grasping portion 3a and an insertion axis of the insertion portion 2 are in a coaxial or parallel positional relation.

An operation input portion 10 (see FIG. 2) configured to perform an operation input for bending the bending portion 2b is provided on an inner side covered with a cover member 7 in the operation portion main body 3b. A bar-like shaft portion 5a of a manipulator 5 configuring the operation input portion 10 projects from the cover member 7. The manipulator 5 is provided to project in a Z-axis direction orthogonal to a longitudinal axis (a Y-axis direction in FIG. 2) of the operation portion main body 3b (or the operation portion 3) from a manipulator projection port, which is an opening, provided on one surface of the operation portion main body 3b. Note that the cover member 7 water-tightly closes the manipulator projection port and closely attaches to the shaft portion 5a of the manipulator main body 5 and is formed of a flexible member such as rubber for holding the manipulator 5 to enable tilting operation of the manipulator 5.

The longitudinal axis of the operation portion main body 3b and the longitudinal axis of the grasping portion 3a are in a coaxial or parallel positional relation.

According to tilting operation including a tilting direction in the up-down direction and the left-right direction and a tilting angle of the manipulator 5 by an operator such as a surgeon, bending operation wires (hereinafter abbreviated as bending wires) 8u, 8d, 8l, and 8r explained below functioning as a traction member inserted through the insertion portion 2 are towed and slacked. The bending portion 2b is configured to be able to be bent in an upward direction, a downward direction, a left direction, and a right direction on a towed side of the bending wires and arbitrary directions among the directions.

In the present embodiment, the bending portion 2b is configured to be bendable in four directions of up, down, left, and right. According to the configuration, the present embodiment includes a traction member in the up-down direction and a traction member in the left-right direction. The manipulator 5 has functions of a manipulator in the up-down direction that is tilted in the up-down direction and a manipulator in the left and right direction that is tilted in the left-right direction. The present invention is not limited to the configuration in which the bending portion 2b bends in the four directions of up, down, left, and right and may be a configuration in which the bending portion 2b bends only in the up-down direction or the left-right direction. The signs u, d, l, and r represent that the signs correspond to the up, down, left, and right directions, which are the bending directions of the bending portion 2b. In the following explanation, for example, a sign 8u represents a bending wire for upward direction. The same applies to the other signs.

For example, in rotating bodies 9u, 9d, 9l, and 9r explained below, for example, 9d represents a rotating body for downward direction. The same applies to the other components.

For example, when this applies to respective bending wires in the bending wires 8u, 8d, 8l, and 8r, the bending wires are represented as bending wires 8 or 8i (i=u, d, l, or r).

Figure 2:
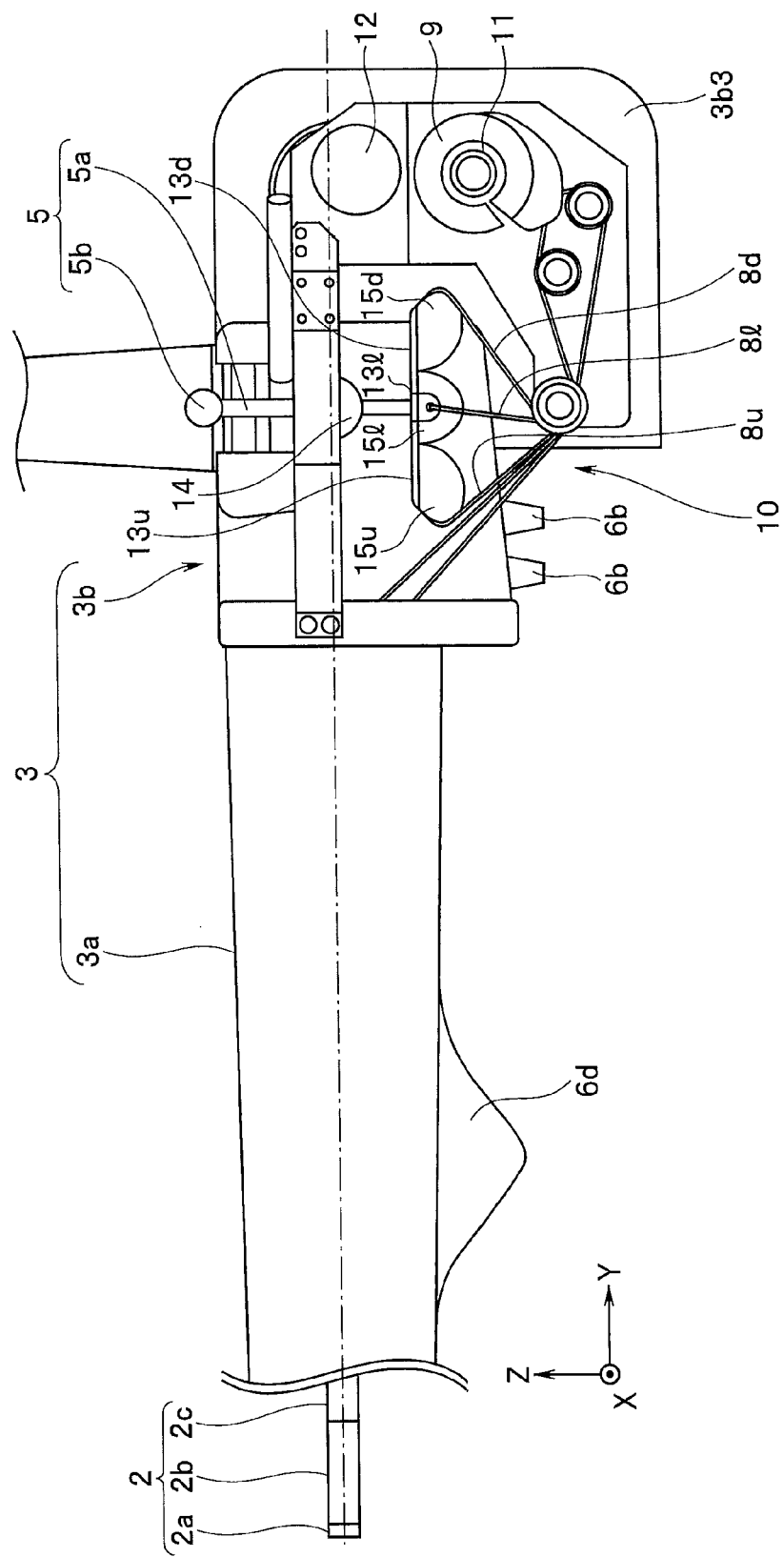
FIG. 2 is a side view showing a configuration around an operation portion provided with an operation input portion in a state in which a side cover of an operation portion main body is grasped.

In an armor of the operation portion main body 3b, besides the manipulator 5, an air feeding and water feeding button 6b and a suction button 6c are provided to project to a position set in advance as shown in FIG. 2. A channel insertion port 6d communicating with a treatment instrument channel (not shown in the figure) is provided near the proximal end of the grasping portion 3a.

When the operator grasps the grasping portion 3a of the operation portion 3 with a left hand in the same manner as grasping a conventional endoscope, the manipulator 5 is provided in a position where the manipulator 5 can be operated to be tilted by a thumb of the grasping hand of the operator and the air feeding and water feeding button 6b and the suction button 6c are provided in a position where the buttons can be operated by a finger other than the thumb of the grasping hand of the operator.

Next, a configuration of the operation input portion 10 is explained with reference to FIGS. 2 to 6. Distal ends of the bending wires 8i inserted through along the respective directions of up-down and left-right in the insertion portion 2 are fixed to a not-shown bending piece at a most distal end configuring the bending portion 2b.

Rear end sides of the bending wires 8i inserted through the insertion portion 2 are coupled to a hanging arm 13 functioning as a coupling member provided at the proximal end of the manipulator 5 through a guide roller set or the like configuring the operation input portion 10.

The operation input portion 10 mainly includes the four bending wires 8u, 8d, 8l, and 8r, the four rotating bodies 9u, 9d, 9l, and 9r, a pulley 11, a motor 12, the manipulator 5 coupled to the hanging arm 13, a plurality of guide roller sets 41, 42, 43, and 44 and a guide roller set 21 configured to change traveling routes of the four bending wires 8u, 8d, 8l, and 8r in the operation portion 3, and wire guides 15u, 15d, 15l, and 15r forming an operation force amount adjusting portion configured to adjust an operation force amount.

The manipulator 5 includes the bar-like shaft portion 5a and a finger rest portion 5b that is formed in a spherical shape at an end portion on a terminal end side of the shaft portion 5a and against which a finger of the operator is pressed. A universal joint 14 forming a bearing configured to rotatably support the shaft portion 5a according to up-down and left-right tilting with respect to the manipulator 5 is provided halfway in the shaft portion 5a. A hanging frame or the hanging arm 13 having a cross shape and extending in the four directions in a plane orthogonal to the shaft portion 5a is coupled and fixed to an end on a proximal end side (a proximal end) of the shaft portion 5a.

At terminal end portions of hanging arms 13u, 13d, 13l, and 13r in the four directions in the hanging arm 13, wire fixing portions 13u2, 13d2, 13l2, and 13r2 (see FIG. 3, etc.), formed by, for example, hole portions, configured to respectively fix (attach) respective proximal ends of the bending wires 8u, 8d, 8l, and 8r are respectively provided. Respective hand side end portions (proximal ends) of the bending wires 8i are fixed at the terminal end portions to be inserted through the hole portions of the wire fixing portions 13i2.

In the present embodiment, near the wire fixing portions 13i2 of the hanging arms 13i, wire guides 15i forming an operation force amount adjusting portion configured to adjust an operation force amount in tilting the manipulator 5 and bending the bending portion 2b are provided.

Note that the manipulator 5 and the hanging arm 13 functioning as the coupling member jointly provided to the proximal end side of the manipulator 5 may be defined as a manipulator or may be defined as separate members.

In the present embodiment, the pulley 11 and the motor 12 are arranged in the operation portion main body 3b in a positional relation in which each of a longitudinal axis of the pulley 11 and a driving axis of the motor 12 is orthogonal to the longitudinal axis of the operation portion 3 (the grasping portion 3a) and such that the longitudinal axis of the pulley 11 and the driving axis of the motor 12 are orthogonal to an axis direction of the manipulator 5 in a state of a neutral position (a neutral state position) as well. The pulley 11 and the motor 12 are separate bodies. The pulley 11 and the motor 12 are disposed, for example, in a position parallel to the axis direction of the manipulator 5 (in FIG. 2, adjacent in the up-down direction near a right end in the operation portion main body 3b).

A motor side gear (not shown) is provided in a shaft (not shown) of the motor 12. A pulley side gear 49 (see FIG. 4) configured to mesh with the motor side gear is provided in a position set in advance of the pulley 11. Rotation of the motor 12 is transmitted to the pulley 11 via the motor side gear and the pulley side gear 49, whereby the motor 12 rotates. Then, the pulley 11 also rotates.

Figure 3:
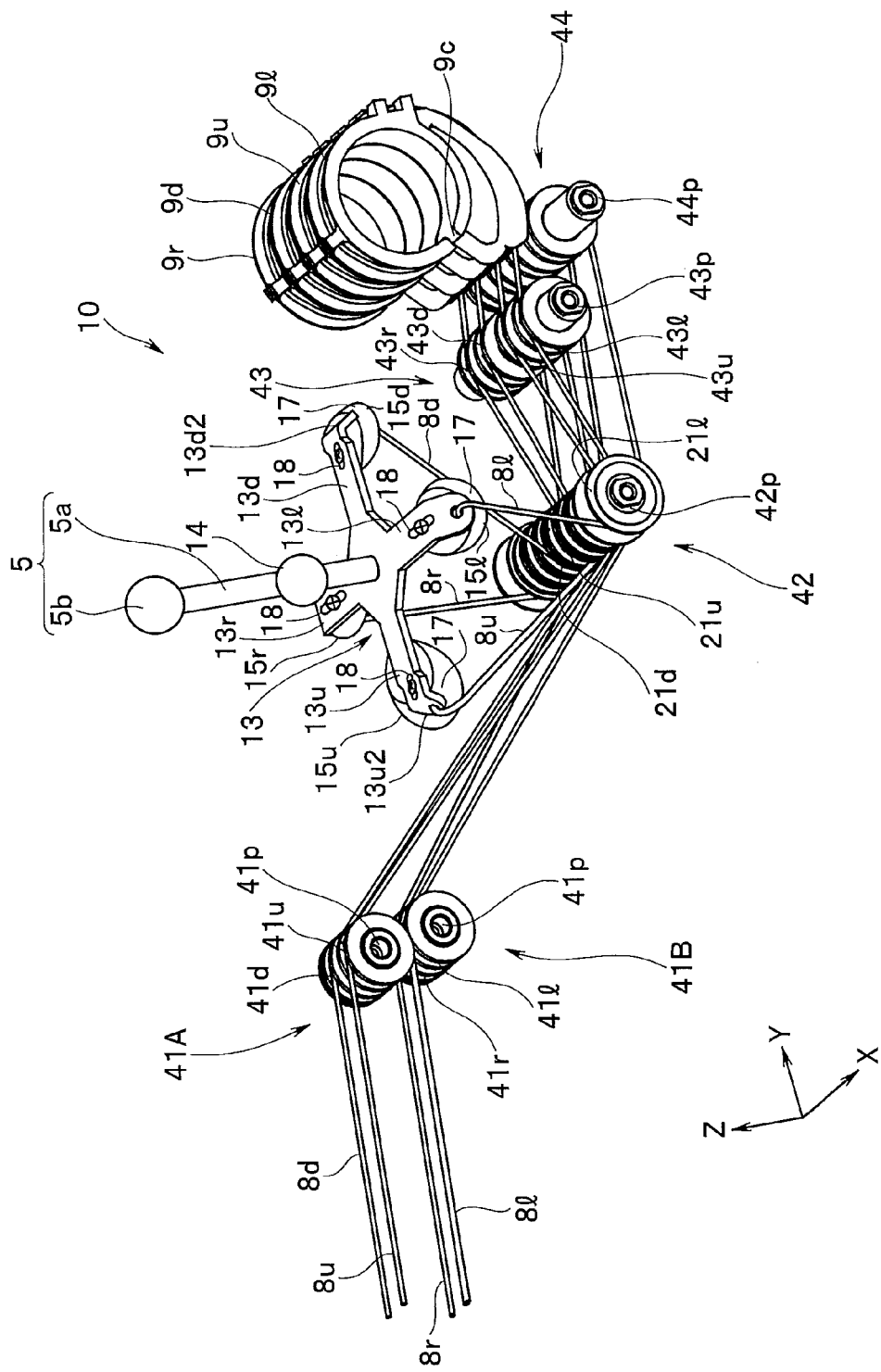
FIG. 3 is a perspective view showing a configuration of the operation input portion including a manipulator or the like for towing a traction member.
Figure 4:
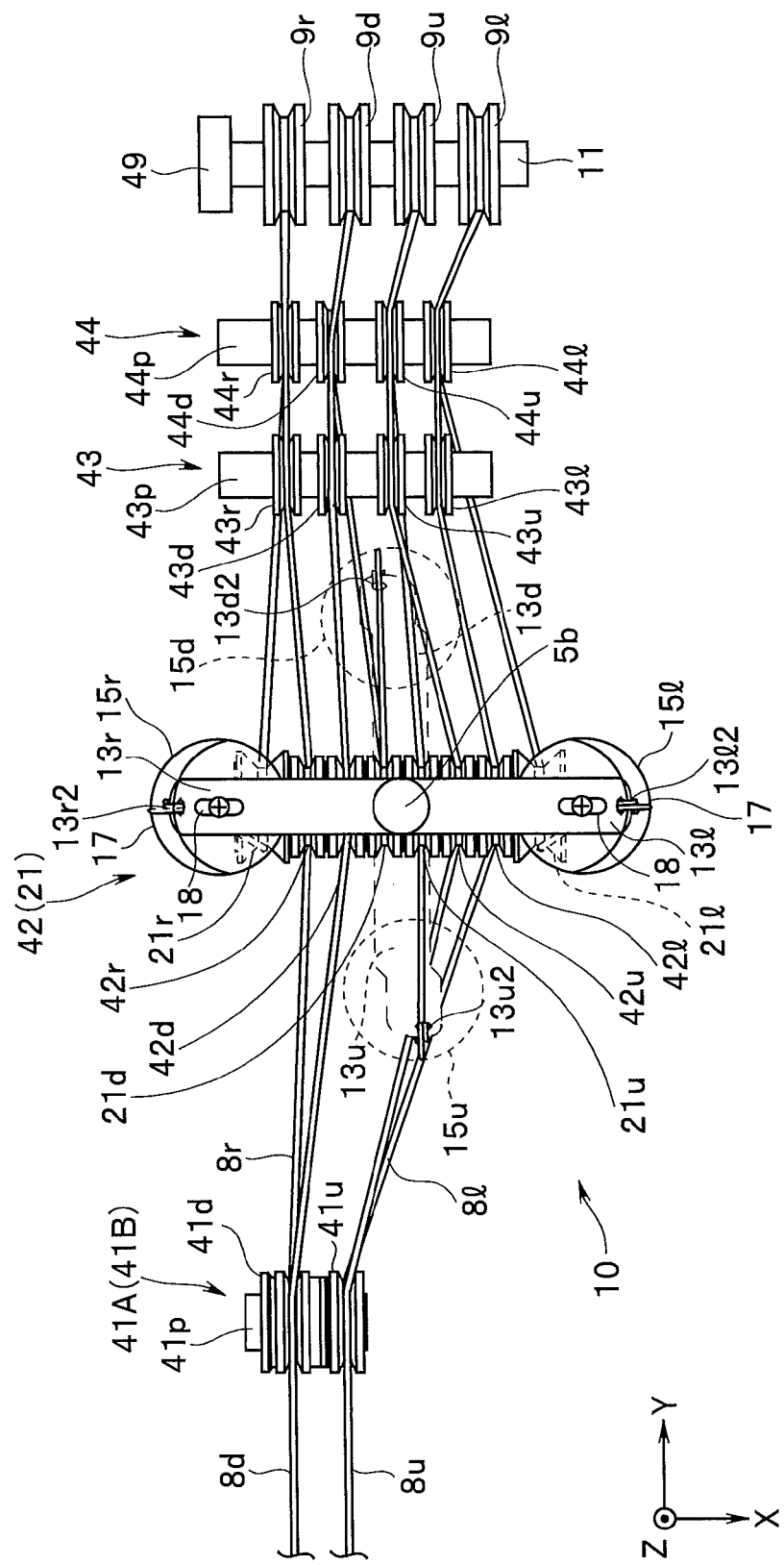
FIG. 4 is a top view showing the configuration of the operation input portion including the manipulator or the like for towing the traction member.

Note that in FIGS. 3 and 4, the motor 12 is not shown. In FIG. 4, portions of the hanging arm for upward direction 13u and the hanging arm for downward direction 13d of the hanging arm 13 are indicated by broken lines. In FIG. 4, in the top view, the pulley 11 in which the rotating bodies 9u, 9d, 9l, and 9r are arranged is shown with positions thereof shifted in the right direction in the figure from the fourth guide roller set 44 (which overlaps the pulley 11 in the top view) to show the traveling routes of the bending wires 8u, 8d, 8l, and 8r.

The traveling routes of the bending wires 8i extended from the distal end side of the insertion portion 2 to the proximal end side thereof are changed to a direction of the second guide roller set 42, which is arranged on a lower side in the axis direction of the manipulator 5, by a first guide roller sets 41A and 41B arranged in the grasping portion 3a.

The traveling routes of the bending wires 8i passed through the second guide roller set 42 are further changed to a direction of the rotating body 9 of the pulley 11 by the third guide roller set 43. The traveling routes of the bending wires 8i passed through the rotating body 9 are changed to a direction of the third guide roller set 42.

The bending wires 8i passed through the third guide roller set 42 pass through the guide roller set 21 coaxially provided with the third guide roller set 42. The bending wires 8i respectively come into contact with the wire guides 15i having a shape close to a substantial semispherical shape forming the operation force amount adjusting portion and respective rear ends of the bending wires 8i are fixed to the wire fixing portions 13i2 provided at cross-shaped end portions of the hanging arm 13 provided at the proximal end of the manipulator 5.

Figure 5:
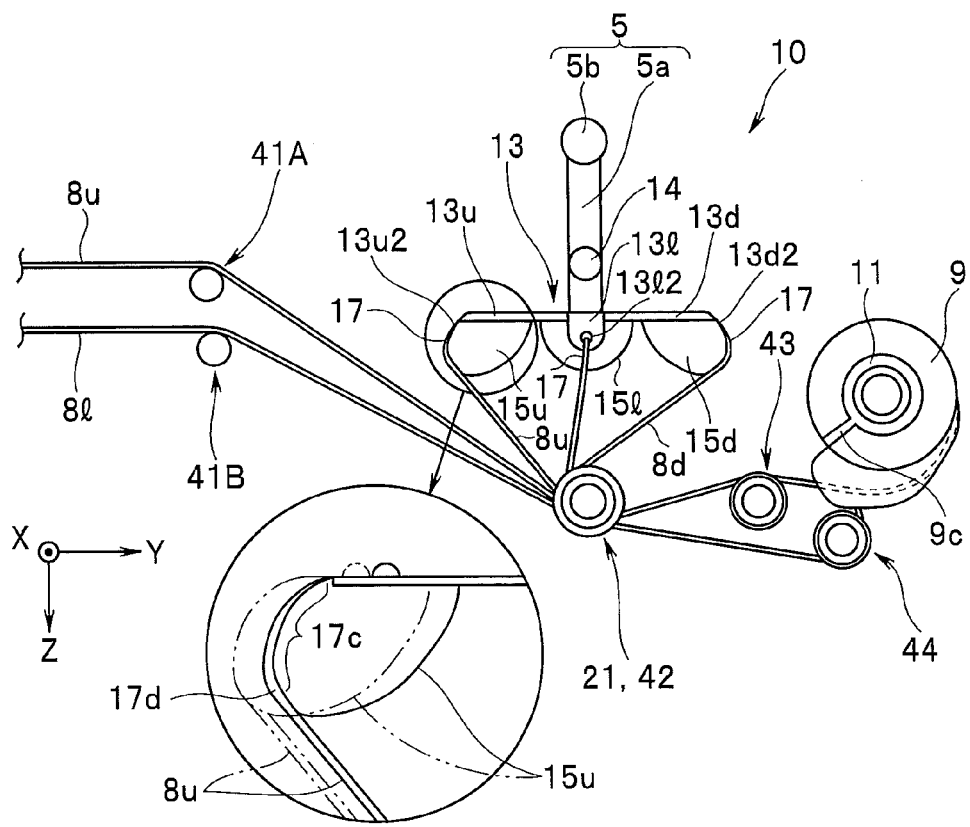
FIG. 5 is a side view of the operation input portion shown in FIG. 3.
Figure 7:
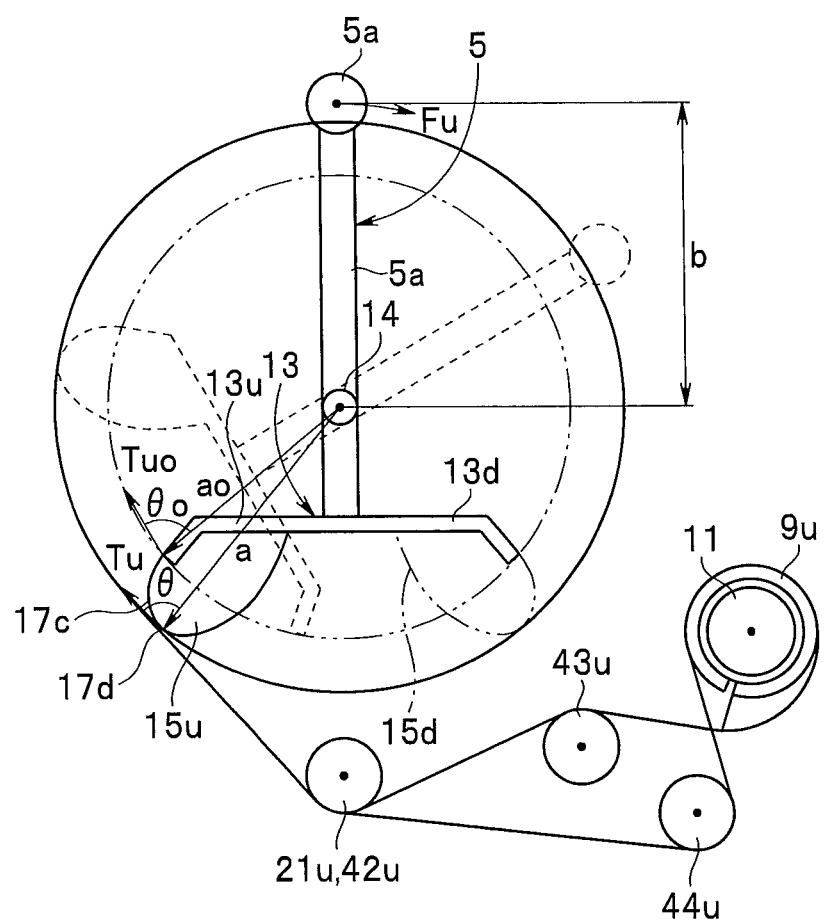
FIG. 7 is an explanatory diagram of action in tilting the manipulator in an upward direction in a simplified form of FIG. 5.

Note that, in FIG. 7 serving as an explanatory diagram close to FIG. 5, the wire guide 15d in an opposite direction of the wire guide 15u is indicated by a broken line to make it easy to distinguish a difference between a case in which the wire guide 15d is provided and a case in which the wire guide 15d is not provided.

As shown in FIGS. 3 to 5, the first guide roller sets 41A and 41B are arranged adjacent to each other along a direction (a Z direction) substantially parallel to the axis direction of the manipulator 5. Each of the first guide roller sets 41A and 41B rotatably supports two guide rollers 41u and 41d or 41l and 41r with a roller shaft 41p.

The bending wires 8u, 8d, 8l, and 8r are guided to the guide rollers 42u and 42d and 42l and 42r of the guide roller set 42, which are arranged on the proximal end side of the manipulator 5, by the guide rollers 41u and 41d and 41l and 41r. The respective guide rollers 42i of the guide roller set 42 are rotatably supported by a common roller shaft 42p together with guide rollers 21i of the guide roller set 21.

The respective bending wires 8i, the traveling routes of which are changed by the respective guide rollers 42i, pass through respective guide rollers 43i rotatably supported by a roller shaft 43p and are guided to the elastic rotating bodies 9i having a C-ring shape pivotably arranged in an outer circumference of the pulley 11.

In a normal state, the rotating bodies 9i pivotably arranged in the outer circumference of the pulley 11 rotated by the motor 12 are in a loosely fit state in which there are slight gaps between the rotating bodies 9i and an outer circumferential surface of the pulley 11 to prevent a friction force from acting. When the bending wires 8i wound around the rotating bodies 9i are towed, a diameter of the rotating bodies 9i is reduced by a traction force amount (a traction force) of the towing. The rotating bodies 9i change to a state in which inner circumferential surfaces of the rotating bodies 9i come into contact with the outer circumferential surface of the pulley 11 and a friction force acts.

In the state in which the friction force acts, the rotating bodies 9i rotate together with the pulley 11 in a direction in which the bending wires 8i are towed and assist(support) a towing action for the bending wires 8i. As shown in FIG. 3 and the like, the rotating bodies 9i are formed in a C-ring shape having a cutout 9c, which is formed by cutting out one place in the circumferential direction in an annular shape, to be easily reduced in diameter when the bending wires 8i are towed.

The respective bending wires 8i wound around the rotating bodies 9i about once are arranged on a lower side along the Z direction of the rotating bodies 9i. The traveling routes of the bending wires 8i are changed by guide rollers 44i rotatably supported by a roller shaft 44p.

The respective bending wires 8i, the traveling routes of which are changed by the guide rollers 44i, passes through the respective guide rollers 21i rotatably supported by the roller shaft 41p and the traveling routes thereof are changed. The bending wires 8i reach the wire fixing portions 13i2 in the hanging arms 13i.

The bending wires 8i extending from the guide rollers 21i to the wire fixing portions 13i2 come into contact with curved surfaces of the wire guides 15i, which are attached near the wire fixing portions 13i2 in the hanging arms 13i, in the traveling routes immediately before the bending wires 8i reach the wire fixing portions 13i2.

Figure 6:
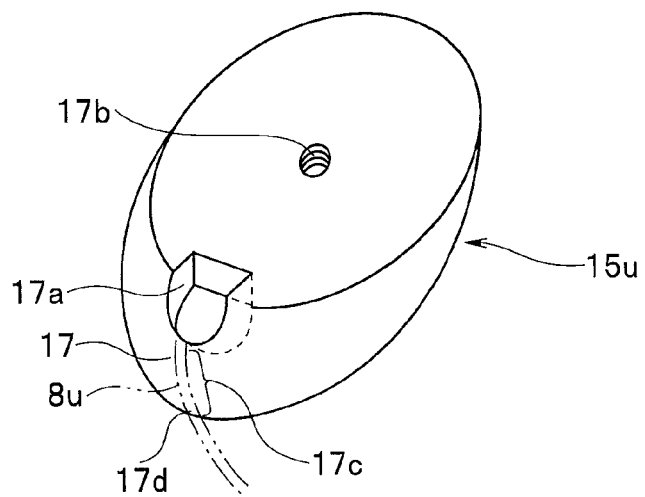
FIG. 6 is a perspective view showing a schematic shape of a wire guide.

FIG. 6 shows a schematic shape of the wire guide 15u in which a contact portion 17c is formed by a projecting surface 17. Note that shapes of the other wire guides 15d, 15l, and 15r are the same as the shape of the wire guide 15u. The wire guide 15u having rigidity is divided into two along a surface passing near a center of a member having a shape close to an ellipsoid (including a sphere). The projecting surface 17 is formed by swelling an outer surface of one end portion in a major axis or minor axis direction of the wire guide 15u. A shape viewed from a side direction orthogonal to a portion where the projecting surface 17 is provided is a fan shape as shown in FIG. 5 and the like.

A concave portion 17a for receiving bent end portions of the hanging arms 13i is provided near an upper surface on the projecting surface 17 in the wire guide 15u. For example, a screw hole 17b is formed near a substantial center in a longitudinal direction of the projecting surface 17 such that the longitudinal direction on the upper surface formed as a plane comes into contact with bottom surfaces of the hanging arms 13i and can be attached (fixed) to the hanging arms 13i. Note that an alternate long and two short dashes line indicates a state in which the bent end portions of the hanging arms 13i are housed in the concave portion 17a and a vicinity of a hand side end portion of the bending wire 8u comes into contact with the projecting surface 17 to form the contact portion 17c. The contact portion 17c, with which the vicinity of the hand side end portion of the bending wire 8u actually comes into contact, moves according to a tilting angle of the manipulator 5. More strictly, the contact portion 17c, with which the vicinity of the hand side end portion of the bending wire 8u actually comes into contact, is a linear range along an extending direction of the bending wire 8u. The range changes according to the tilting angle of the manipulator 5. An operation force amount necessary for tilting operation of the manipulator 5 can be adjusted by an acting position 17d where a traction force acts on the bending wire 8u in the contact portion 17c as explained below. Note that the acting position 17d where the traction force acts on the bending wire 8u in the contact portion 17c can also be represented as a position with which the bending wires 8i functioning as the traction member come into contact at a largest distance from a rotation axis in the contact portion 17c with which the bending wires 8i come into contact. In the case of FIGS. 5, 6, and 7, an end portion on a lower end side in the linear range of the contact portion 17c is the acting position 17d.

On the other hand, in the hanging arms 13i, long holes 18 are provided along a longitudinal direction thereof to make it possible to adjust an attaching position of the wire guide 15u to a longitudinal direction of the long holes 18.

When the wire guides 15i are attached to the hanging arms 13i, the projecting surface 17 adjacent to a lower side of the concave portion 17a comes to be a contact surface or the contact portion 17c that comes into contact with the bending wires 8i.

A position where the wire guide 15 is attached in the longitudinal direction of the hanging arms 13i is changed within a range of length of the long holes 18 attached to the hanging arms 13i. Consequently, it is possible to easily adjust an operation force amount by changing a distance to the acting position 17d of the contact portion 17c in the wire guides 15i, with which the hand side end portions of the bending wires 8i come into contact from the universal joint 14 when the manipulator 5 is tilted and which transmits an operation force amount by the tilting operation of the manipulator 5 as a traction force (a traction force amount).

The operator places a finger of the hand grasping the grasping portion 3a in the finger rest portion 5b of the manipulator 5 to tilt the shaft portion 5a of the manipulator 5. Consequently, the manipulator 5 tilts with a rotation center (a tilting center) set in a position where the manipulator 5 is pivotably supported by the universal joint 14 functioning as a bearing with respect to the up-down and left-right directions.

In this case, according to the tilting of an upper end side of the manipulator 5, a hanging arm 13j (j represents a specific hanging arm corresponding to the tilting of the upper end side of the manipulator 5) at the lower end side corresponding to the tilting of the upper end side of the manipulator 5 also tilts. According to the tilting of the hanging arm 13j, a bending wire 8j is towed. A rotating body 9j around which the bending wire 8j is wound is reduced in diameter by the towed bending wire 8j.

As explained above, according to the reduction in diameter, the rotating body 9j comes into contact with a pulley 11j on an inner side thereof (which transmits a rotating force of the motor 12). A friction force acts on the rotating body 9j and the pulley 11j and moves the bending wire 8j in a rotating direction of the pulley 11j. According to the movement, the bending portion 2b, to which a distal end of the bending wire 8j is fixed, can be bent in a bending direction corresponding to operation of tilting of the manipulator 5.

By providing the wire guides 15i, an operation force amount in tilting the manipulator 5 can be adjusted by changing a distance in which a traction force amount for traction acts on the bending wires 8i.

As explained below with reference to FIG. 7, the operation force amount can be adjusted by changing the distance from a distance $a_0$ (a first distance) in which a traction force amount acts on the hand side end portions of the bending wires 8i according to the tilting operation of the manipulator 5 when the wire guides 15i are not provided to a distance a (a second distance) in which the traction force acts when the wire guides 15i are provided.

The endoscope 1 in the present embodiment having such a configuration is characterized by including the insertion portion 2 including the bending portion 2b, the bending wires 8i functioning as the traction member for bending the bending portion 2b through traction, the operation portion 3 provided at the proximal end of the insertion portion 2 and provided with the operation input portion 10 for performing an operation input for bending the bending portion 2b, the manipulator 5 including the hanging arms 13i functioning as the coupling members configuring the operation input portion 10 and provided to correspond to the bending direction of the bending portion 2b to which the traction member is coupled, the manipulator 5 pivoting around the rotating shaft pivotably supported by the universal joint 14 provided in the operation portion 3 according to tilting operation for performing the operation input and towing the traction member in the tilting direction, and the operation force amount adjusting portion configured to act on the traction member according to the tilting operation of the manipulator 5 and adjust an operation force amount necessary for the tilting of the manipulator 5.

More specifically, the operation force amount adjusting portion can be configured by the wire guides 15i including the projecting surface 17 forming the contact portion 17c that brings the operation force amount adjusting portion into contact with the traction member extending from the coupling member and transmits an operation force amount by the tilting of the manipulator 5 to the traction member and configured to adjust an operation force amount necessary for the tilting of the manipulator 5 by changing the first distance $a_0$ between the position where the traction member is coupled in the coupling member and the rotating shaft to the second distance a between the acting position 17d where the traction force acts on the traction member in the contact portion 17c and the rotating shaft simultaneously with the tilting of the manipulator 5.

Note that, as explained with reference to FIG. 11 below, instead of configuring the operation force amount adjusting portion with the wire guides 15i configured to change the first distance $a_0$ to the second distance a between the acting position 17d in the contact portion 17c and the rotating shaft and adjust the operation force amount necessary for the tilting of the manipulator 5, it is also possible to configure the operation force amount adjusting portion including springs 51i provided in the manipulator 5 and functioning as elastic bodies for elastically urging the traction member extending from the coupling member with respect to the tilting of the manipulator 5 and configured to adjust the operation force amount necessary for the tilting of the manipulator 5 by elastically changing, with the elastic member, an acting direction of a traction force acting on the traction member extending from the coupling member.

Next, action in the present embodiment is explained with reference to FIG. 7. FIG. 7 is a side view viewed from the same side direction as FIG. 5. In the figure, an explanatory diagram is shown in which, when the manipulator 5 is tilted in a state in which the manipulator 5 is viewed from a side direction perpendicular to a plane including the shaft portion 5a of the manipulator 5 in a neutral position state and the hanging arms 13u and 13d of the manipulator 5, the manipulator 5 tilts with a rotation center or a rotation axis set in a position pivotably supported by the universal joint 14 in the shaft portion 5a of the manipulator 5. Note that, in FIG. 7, only a guide roller related to the upward direction in the guide roller set indicated by sign 42 or the like is shown (the same applies in modifications and embodiments explained below).

In FIG. 7, an operation force amount obtained when the operator places a finger in the finger rest portion 5b of the manipulator 5 and tilts the shaft portion 5a in the upward direction in order to bend the bending portion 2b in the upward direction is represented as Fu, a distance from a center of the universal joint 14 to the acting position (or the contact portion acting position) 17d where the vicinity of the hand side end portion of the bending wire for upward direction 8u comes into contact in the contact portion 17c and a traction force amount Tu for towing the bending wire 8u for upward direction acts in the wire guide for upward direction 15u is represented as a, and a distance (also referred to as operation side distance) from the center of the universal joint 14 to a center of the finger rest portion 5b is represented as b.

A distance from the center of the universal joint 14 to (a terminal end position of) the wire fixing portion for upward direction 13u2, which is a position where a traction force amount $Tu_0$ for towing the bending wire for upward direction 8u in the case in which the wire guide for upward direction 15u is not provided is represented as $a_0$.

In FIG. 7, a circle indicated by a solid line indicates a track drawn by the acting position 17d when the manipulator 5 is tilted. A circle indicated by an alternate long and two short dashes line indicates a track drawn by the wire fixing portion for upward direction 13u2 when the manipulator 5 is tilted.

In a state in which the operation force amount Fu in the upward direction and the traction force amount Tu for towing the bending wire for upward direction 8u are balanced when the manipulator 5 is tilted with the operation force amount Fu in the upward direction, the following Equation (1) holds:

$$Fu \times b = Tu \times a \sin \theta \quad (1)$$

where θ represents an angle formed by a direction from the center of the universal joint 14 to the acting position 17d and a direction of the traction force amount Tu.

On the other hand, in the case of the related art in which the wire guide for upward direction 15u is not provided, in the balanced state, the following Equation (2) holds:

$$Fu \times b = Tu_0 \times a_0 \sin \theta_0 \quad (2)$$

where, $\theta_0$ represents an angle formed by a direction from the center of the universal joint 14 to a wire fixing portion and a direction of a traction force amount $Tu_0$.

As it is evident from FIG. 7, when the tilting operation is performed by the wire guide for upward direction 15u, the distance a acting as the traction force amount Tu for towing the bending wire for upward direction 8u is larger even when the tilting angle is changed than in the case in which the wire guide for upward direction 15u is not provided.

The angle θ is larger than the angle $\theta_0$ in a tilting range (a bending range). In the case of FIG. 7, θ (and $\theta_0$) is smaller than 90°. Therefore, $\sin \theta > \sin \theta_0$.

When magnitudes of the traction force amounts Tu and $Tu_0$ are set the same, a larger operation force amount is necessary when the wire guide for upward direction 15u is provided than when the wire guide for upward direction 15u is not provided.

When the endoscope 1 does not include the wire guide for upward directions 15i, an operation force amount necessary in the tilting operation to bend the bending portion 2b near the neutral position may be small (the tilting operation for the bending can be performed with a small operation force amount). Therefore, when small bending is about to be performed, it is necessary to perform the tilting operation with a fine operation force amount.

On the other hand, when the wire guides 15i are provided, the distance a larger than the distance $a_0$ when the wire guides 15i are not provided is set. Therefore, it is possible to perform the same tilting operation with a rougher operation force amount. It is possible to reduce a burden on the operator with a simple configuration and improve operability. Even when the operation portion 3 is reduced in size by, for example, reducing a length of the shaft portion 5a of the manipulator 5, it is possible to provide the endoscope 1 that can adjust an operation force amount. Further, by increasing an operation force amount near the neutral position (necessary for the tilting operation for bending the bending portion 2b), it is possible to prevent the bending portion 2b from being bent by careless tilting operation.

Figure 8:
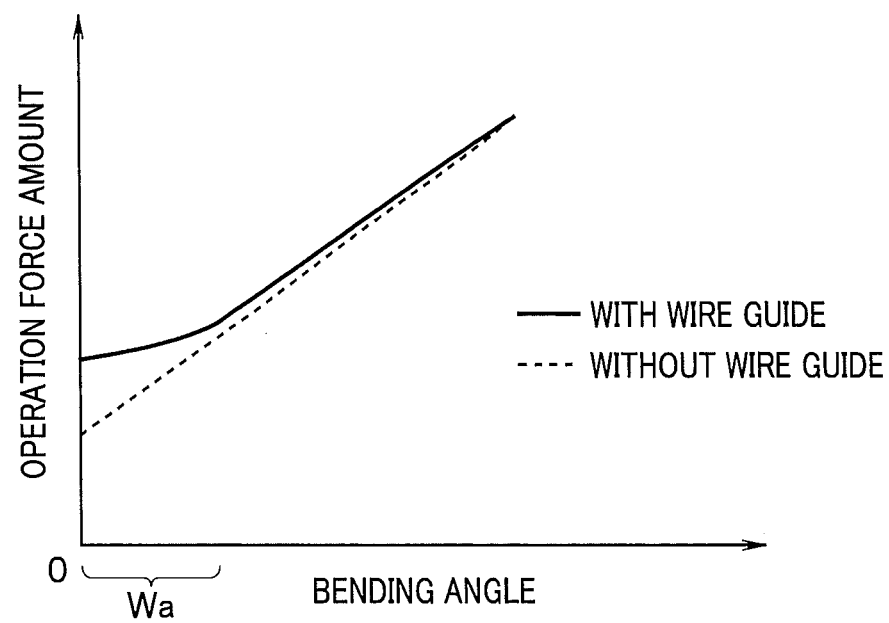
FIG. 8 is a characteristic chart showing a relation of an operation force amount with respect to a bending angle.

FIG. 8 shows a characteristic chart showing a relation of an operation force amount (with respect to a bending angle or a tilting angle) necessary when the bending portion 2b in the present embodiment is bent in the upward direction.

Note that, in FIG. 8, a dotted line indicates a characteristic in the case of the related art in which the wire guide 15 is not provided. As it is seen from FIG. 8, when the wire guide 15 is not provided, in a bending range (a tilting range) Wa near the neutral position, the operator needs to finely adjust an operation force amount as explained above. However, according to the present embodiment, since the characteristic requires a larger operation force amount, it is possible to smoothly set the bending angle to a desired bending angle through tilting operation with a rougher operation force amount.

Note that FIGS. 7 and 8 are explained in the case of the tilting operation for performing the bending in the upward direction. However, substantially the same action and effects are obtained in cases of the other directions.

In this way, according to the present embodiment, by providing the wire guides 15i, in particular, it is possible to set a bending force amount in bending the bending portion 2b in a state close to the neutral position to an easily operable value and improve operability.

As shown in an enlarged view of FIG. 5, for example, by changing an attaching position of the wire guide for upward direction 15u from the solid line as indicated by the alternate long and two short dashes line, it is possible to easily perform adjustment for, for example, changing a distance d from a position of a rotation center in performing tilting operation to the contact portion 17c and changing a value of the operation force amount Fu. In the example shown in FIG. 5, it is possible to increase the value of the operation force amount Fu. If the attaching position of the wire guide for upward direction 15$u$ is shifted in an opposite direction, it is possible to reduce the value of the operation force amount Fu. Note that it is possible to adjust operation force amounts in the other directions in the same manner.

Note that the shape of the wire guides 15$i$ is one example and may be a shape different from the shape shown in the figure. In the example explained above, the wire guides 15$u$, 15$d$, 15$l$, and 15$r$ are provided in both of the up-down direction and the left-right direction. However, the wire guides 15$u$ and 15$d$ or 15$l$ and 15$r$ may be provided only in at least one of the up-down direction and the left-right direction.

Figure 9:
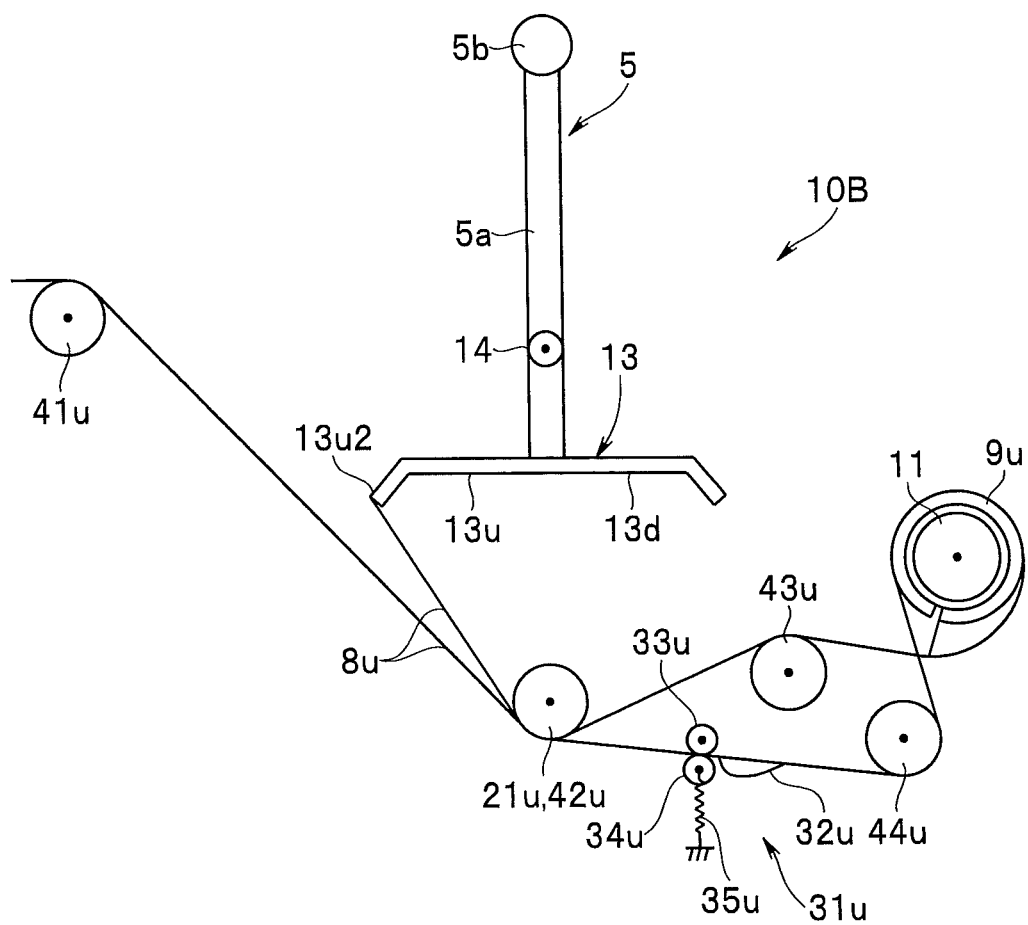
FIG. 9 is a diagram showing a schematic configuration of an operation input portion in a first modification of the first embodiment.

FIG. 9 shows a configuration of a peripheral portion of an operation input portion 10B in a first modification of the first embodiment. In this modification, resistance portions 31$i$ functioning as resistance in towing the bending wires 8$i$ are provided halfway in the traveling routes of the bending wires 8$i$ to form an operation force amount adjusting portion, whereby functions similar to the functions in the first embodiment are provided. Note that a case of i=u is shown in FIG. 9. However, the resistance portions 31$i$ are provided in the same manner in a case of i=d, l, r.

The resistance portion 31$i$ is configured by guide members 32$i$ attached to the bending wires 8$i$, pairs of guide rollers 33$i$ and 34$i$ arranged to sandwich the bending wires 8$i$ on the traveling routes of the bending wires 8$i$ on which the guide members 32$i$ are towed and moved (by tilting operation of the manipulator 5), and springs 35$i$ configured to urge the one guide rollers 34$i$ to the other guide rollers 33$i$ side. One ends of the springs 35$i$ are fixed to an inner wall of the operation portion 3 or a frame for retaining the operation input portion 10B. The other ends are fixed to bearings of the guide rollers 34$i$.

The guide members 32$i$ are set in a shape in which thickness on a distal end side in a direction of traction movement of the bending wires 8$i$ (in FIG. 9, the left direction) is large and decreases toward a rear end side.

Figure 10:
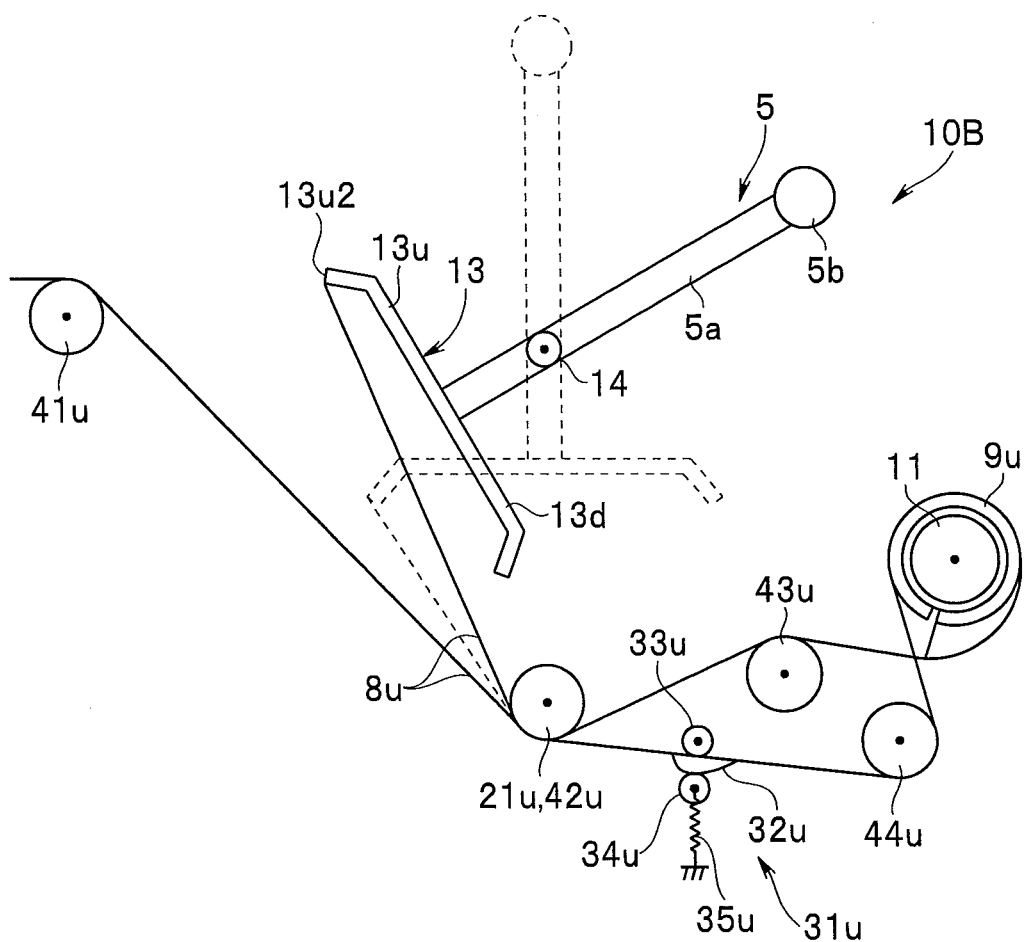
FIG. 10 is a diagram showing a state in which the manipulator is tilted in FIG. 9.

FIG. 10 shows a state in which the manipulator 5 in the neutral position state in FIG. 9 is tilted to the upward direction (tilted in a clockwise direction in FIG. 9) to be bent in the upward direction of the bending portion 2$b$. This modification is the same as a configuration in which the resistance portions 31$i$ are provided in the configuration in which the wire guides 15$i$ are not provided in the first embodiment.

Next, action of this modification is explained. When the operator tilts the manipulator 5, for example, in the upward direction, the hanging arm for upward direction 13$u$ rotates in the clockwise direction from the state shown in FIG. 9. Then, the hand side end portion of the bending wire for upward direction 8$u$ is towed and the bending wire for upward direction 8$u$ moves in a direction in which the hand side end portion is towed.

A guide member for upward direction 32$u$ moves together with the movement of the bending wire for upward direction 8$u$. As shown in FIG. 10, the guide member for upward direction 32$u$ is located between the pair of guide rollers 33$u$ and 34$u$. In this state, the guide member for upward direction 32$u$ passes between the guide rollers 33$u$ and 34$u$ while being pressed by the pair of guide rollers 33$u$ urged by the spring for upward direction 35$u$.

In this case, the guide member 32$u$ functions as resistance for traction movement of the bending wire for upward direction 8$u$. As a result, an operation force amount necessary in tilting the manipulator 5 is increased. In this modification, resistance against traction movement is large in a state in which the guide member 32$u$ nearly starts to come into contact with the guide rollers 33$u$ and 34$u$. Thereafter, the resistance decreases according to the traction movement.

Therefore, in this modification, by arranging the guide member 32$u$ near the guide rollers 33$u$ and 34$u$ as shown in FIG. 9, it is possible to increase an operation force amount in performing tilting operation near a bending range Wa closer to the neutral position of the manipulator 5. This modification has effects similar to the effects in the first embodiment.

Note that, in the example shown in FIG. 9, the guide members 32$i$ (i=u) have a rotation-asymmetrical shape in which width changes in directions of the opposed guide rollers 33$i$ and 34$i$ in the bending wires 8$i$. However, the guide members 32$i$ may be formed in a rotation-symmetrical shape around the bending wires 8$i$.

This modification may be applied to the first embodiment as well. When this modification is applied to the first embodiment, there is an effect that adjustment of an operation force amount can be performed in a wider range.

By adjusting shapes and arranging positions of the guide rollers 33$i$ and 34$i$ and the guide members 32$i$, it is also possible to adjust an operation force amount in a desired bending range not only in the bending range Wa near the neutral position of the manipulator 5 but also in a bending range in a wider range.

Shapes on a distal end side and a rear end side in the direction of traction movement shown in FIG. 9 may be reversed to set thickness on the distal end side in the direction of traction movement to be small and increase toward the rear end side. In this case, it is possible to set (adjust) an operation force amount such that the operation force amount near the bending range Wa close to the neutral position is small and the operation force amount is large on a bending range side deviating from the bending range Wa.

Note that, in the first embodiment and the first modification, the operation force amount adjusting portion is explained that adjusts (sets) the operation force amount to be large in the bending range close to the neutral position or the tilting range for performing operation of bending. However, the present invention is not limited to such a case.

For example, in the case of a use for mainly performing large bending operation, if an operation force amount in performing small bending is reduced, it is possible to reduce a burden on the operator in performing tilting operation.

In relation to such a case, as explained below, an operation force amount adjusting portion may be formed that reduces an operation force amount on a bending range side close to the neutral position.

Figure 11:
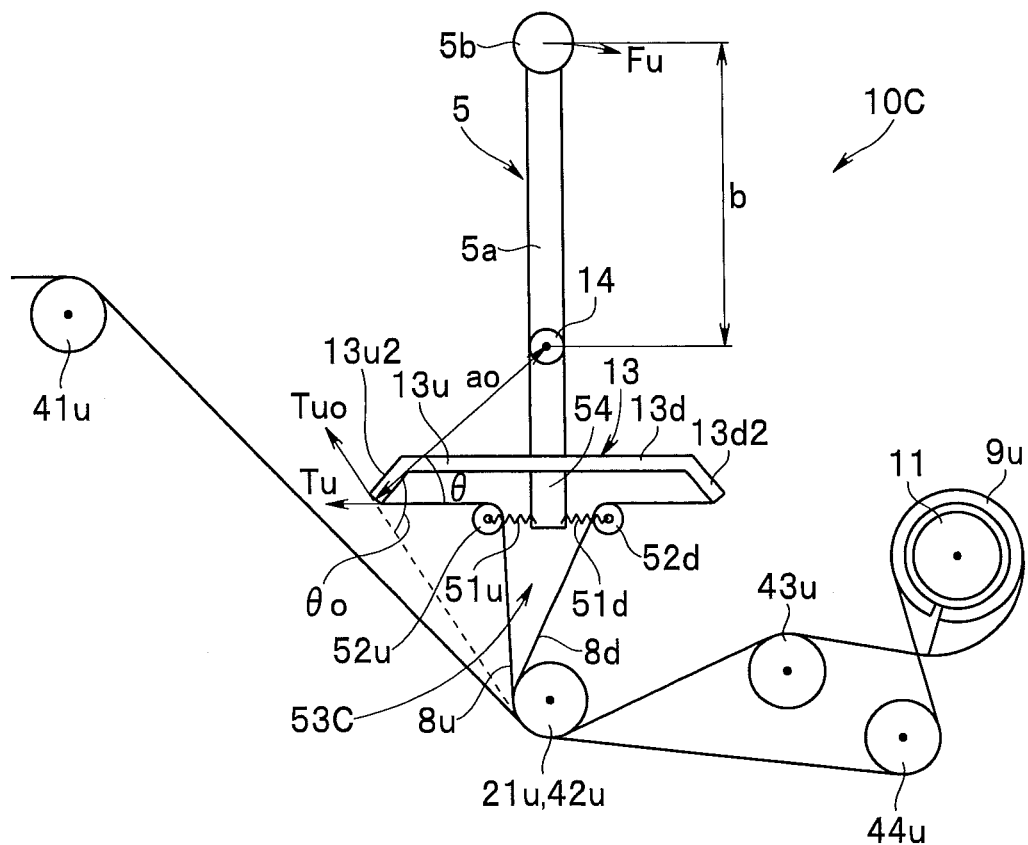
FIG. 11 is a diagram showing a schematic configuration of an operation input portion in a second modification of the first embodiment.

FIG. 11 shows a configuration of a peripheral portion of an operation input portion 10C in a second modification of the first embodiment. In this modification, as in the first modification, an operation force amount adjusting portion 53C is formed using the springs 51$i$ and the guide rollers 52$i$ coupled to the manipulator 5 instead of providing the wire guides 15$i$ in the first embodiment.

In this modification, the operation force amount adjusting portion 53C is formed that adjusts an operation force amount by changing, with respect to tilting operation of the manipulator 5, using an elastic force of the springs 51$i$, direction of a traction force acting on the hand side end portions of the bending wires 8$i$ functioning as the traction member.

As shown in FIG. 11, a projecting piece 54 projecting downward piercing through a (not-shown) hole of the hanging arm 13 is provided in the manipulator 5. One ends of the springs 51$i$ are fixed to a lower end of the projecting piece 54. In other words, the one ends of the springs 51$i$ functioning as elastic bodies or elastic members are fixed to the proximal end or ends on the proximal end side of the manipulator 5. Note that the projecting piece 54 may be projected from the hanging arm 13. The one ends of the springs 51$i$ may be fixed to, for example, a center position of a bottom surface of the hanging arm 13 functioning as a coupling member without providing the projecting piece 54.

The other ends of the springs 51$i$ are attached to rotating shafts of the guide rollers 52$i$ configured to changeably hold the traveling routes of the bending wires 8$i$ extended from the guide rollers 21$i$ to the wire fixing portions 13$i$2 (the guide roller set 21 side) of the hanging arm 13. The rotating shafts of the guide rollers 52$i$ are movably held in a state in which the rotating shafts pulled to a lower end side of the projecting piece 54 (to which the one ends of the springs 51$i$ are fixed) with an elastic force by the springs 51$i$. In other words, the springs 51$i$ urge the guide rollers 21$i$, to which the other ends of the springs 51$i$ are fixed, to be elastically towed to thereby urge the bending wires 8$i$ in positions where the bending wires 8$i$ are movably held by the guide rollers 21$i$ to be towed to the one end side of the spring 51$i$. Note that, in FIG. 11, springs 51$u$ and 51$d$ and guide rollers 52$u$ and 52$d$ are shown. However, not-shown springs 51$l$ and 51$r$ and guide rollers 52$l$ and 52$r$ are provided in a vertical direction of a paper surface.

In this modification, when the manipulator 5 is tilted in the clockwise direction from the state shown in FIG. 11 (in order to bend the bending portion 2$b$ in the upward direction), the spring 51$u$ extends according to an increase in a traction force amount (an increase in a bending load).

Figure 12:
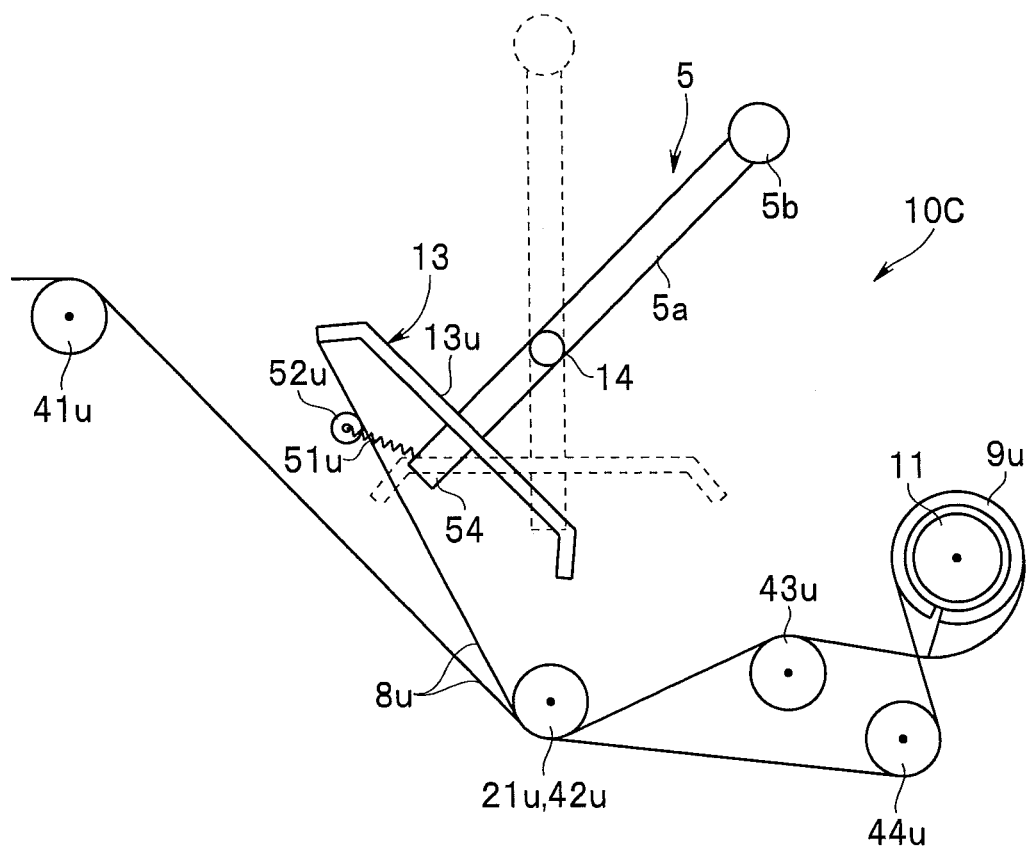
FIG. 12 is a diagram showing a state in which the manipulator is tilted at a predetermined tilting angle or more in FIG. 11.

Therefore, when the manipulator 5 is tilted, for example, at a predetermined angle or more in the upward direction, as shown in FIG. 12, the spring 51$u$ extends because of an increased traction force amount. The bending wire for upward direction 8$u$ extending from the guide roller for upward direction 21$u$ nearly linearly extends from a bent state with an elastic force of the spring 51$u$ to reach the wire fixing portion for upward direction 13$u$2. Note that, in FIG. 12, only members related to the bending wire for upward direction 8$u$ are shown.

In this way, in this modification, the operation force amount adjusting portion 53C is formed to adjust, near the neutral position, with the springs 51$i$, an operation force amount such that the traction force amount for towing the bending wires 8$i$ acts in a different direction (from the related art in which the springs 51$i$ and the guide rollers 52$i$ are not provided), the springs 51$i$ extend as the traction force amount increases, and an operation force amount close to an operation force amount in the related art is obtained.

In particular, the operation force amount adjusting portion 53C is set to a characteristic for making it possible to greatly change, near the neutral position, a direction in which a traction force or a traction force amount acts (from the case of the related art) and bend the bending portion 2$b$ with a smaller operation force amount than the case of the related art. In the state shown in FIG. 11, a traction force amount acting on (the hand side end portion of) the bending wire for upward direction 8$u$ when the manipulator 5 is tilted is Tu along a direction near a horizontal direction of the paper surface as bending wire for upward direction 8$u$ is pulled by the spring 51$u$ in this modification. On the other hand, in the case of the related art in which the spring 51$u$ is not provided, the traction force is Tu$_0$ along a direction indicated by a dotted line.

As explained in the first embodiment, in a state in which the operation force amount Fu in the upward direction and the traction force amount Tu for towing the bending wire 8$u$ in the upward direction are balanced when the manipulator 5 is tilted with the operation force amount Fu in the upward direction, the following Equation (3) holds:

$$Fu \times b = Tu \times a_0 \sin \theta \quad (3)$$

where θ represents an angle (or a supplementary angle) formed by a direction from the center of the universal joint 14 to the wire fixing portion for upward direction 13$u$2 and a direction of the traction force amount Tu. Note that sin θ=sin (180°−θ).

On the other hand, in the case of the related art, in the balanced state, the following Equation (4) holds:

$$Fu \times b = Tu_0 \times a_0 \sin \theta_0 \quad (4)$$

where, $\theta_0$ represents an angle (or an supplementary angle) formed by a direction from the center of the universal joint 14 to the wire fixing portion for upward direction 13$u$2 and a direction of the traction force amount Tu$_0$.

In the case of FIG. 11, since the angle $\theta_0$ is close to 90°, Equation (4) is approximately the following Equation (5).

$$Fu \times b \approx Tu_0 \times a_0 \quad (5)$$

Concerning the case in which the traction force amounts Tu and Tu$_0$ are the same magnitude, in this modification, an operation force amount is adjusted to be sine (more accurately, sin θ/sin $\theta_0$) times as large as an operation force amount in the related art by changing a direction in which a traction force amount acts.

Figure 13:
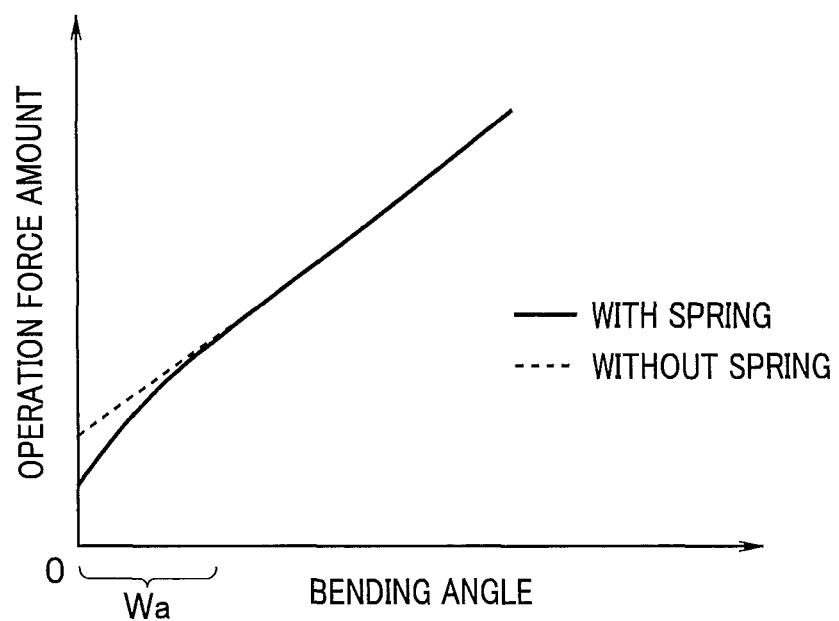
FIG. 13 is a characteristic chart showing a relation of an operation force amount with respect to a bending angle.

In FIG. 13, a schematic characteristic of an operation force amount with respect to a bending angle by this modification is indicated by a solid line and a schematic characteristic in the case of the related art is indicated by a dotted line. As shown in FIG. 13, in the bending range Wa close to the neutral position as shown in FIG. 13, tilting operation is performed with an operation force amount smaller than an operation force amount in the related art.

Note that the characteristic shown in FIG. 13 can be changed by adjusting the elastic force of the springs 51$i$.

According to this modification, it is possible to reduce an operation force amount in performing small bending and reduce a burden on the operator in frequently using larger bending.

FIG. 14 shows a top view (FIG. 14(A)) and a side view (FIG. 14(B)) of a hanging arm coupled to a lower end of a manipulator in a third modification of the first embodiment. In this modification, an integrated wire guide 71 is attached to the hanging arm 13 as shown in FIG. 14.

In the hanging arms 13$i$, long grooves 72$i$ extending long from respective end portions to the shaft portion 5$a$ side of the manipulator 5 on a center side of the hanging arms 13$i$ are formed. In the wire guide 71, wire fixing portions 73$i$ configured to fix (attach) the hand side end portions of the respective bending wires 8$i$ to a vicinity of an upper surface end portion facing an inner side of the long grooves 72$i$ in the wire guide 71 are provided.

As shown in the side view of FIG. 14(B), in the wire guide 71, a size extending to a curved surface in the downward direction is set larger than a size in the horizontal direction. A distance h extending from the rotation center of the manipulator 5 to a curved surface in a periphery in the downward direction is set to a distance a$_0$ extending from the rotation center to the wire fixing portions of the hanging arms 13$i$ (i.e., h=a$_0$). As shown in FIG. 14(B), in a state of the neutral position, a distance extending from the rotation center to the wire fixing portions of the hanging arms 13$i$ is a'. Therefore, a$_0$>a'. Therefore, in the state of the neutral position, in this modification, it is possible to tilt the manipulator 5 and bend the bending portion 2$b$ with a smaller operation force amount than an operation force amount in the case of the related art in which the wire guide 71 is not provided. Similarly, in a small bending range close to the neutral position, it is possible to perform tilting operation for bending the bending portion 2$b$ with a smaller operation force amount than the operation force amount in the case of the related art.

As shown in FIG. 14(B), the bending wire for upward direction 8u extended from the guide roller 21u is fixed to a position of a hand side end portion 73u as indicated by a solid line. On the other hand, an alternate long and two short dashes line indicates a case in which the wire guide 71 is not provided and the bending wire for upward direction 8u is fixed to a wire fixing portion of the hanging arm for upward direction 13u. A radius of an alternate long and short dash line indicates that the distance $a_0$ from the rotation center to the wire fixing portion of the hanging arm for upward direction 13u is set as a radius. In FIG. 14(B), members related to bending in the upward direction are shown. However, the same substantially applies in the case of bending in the downward direction. The same substantially applied in the case of the left-right direction.

Therefore, this modification has a characteristic closer to the characteristic chart of FIG. 13. That is, it is possible to reduce an operation force amount in the case of a small bending range. According to this modification, it is possible to form an operation force amount adjusting portion that can easily adjust an operation force amount. Note that, although the integrated wire guide 71 is used in this modification, the wire guide 71 may be formed by a plurality of wire guides without being integrated.

Second Embodiment

Next, a second embodiment of the present invention is explained with reference to FIG. 15. In the first embodiment explained above, the bending portion 2b can be bent in any bending direction in an up-down direction and a left-right direction by tilting operation by a finger.

When such tilting operation is performed, a bending direction of bending in the up-down direction and the left-right direction is set by giving a difference to magnitudes of operation force amounts, whereby it is possible to easily distinguish (or sense) the bending direction with a finger for performing the tilting operation. Therefore, it is possible to improve operability for an operator.

In the present embodiment, in order to improve operability in this way, an operation force amount necessary in performing tilting operation for bending the bending portion 2b is set to be different in the up-down direction and the left-right direction to be easily distinguished (or sensed).

FIG. 15(A) shows a side view of a peripheral portion of an operation input portion 10D in which the manipulator 5 in a neutral position state is viewed from a longitudinal direction of the hanging arm for left direction 13l. FIG. 15(B) shows a side view of a peripheral portion of an operation input portion 10E in which the manipulator 5 in the neutral position state is viewed from a longitudinal direction of the hanging arm for upward direction 13u.

Figure 15:
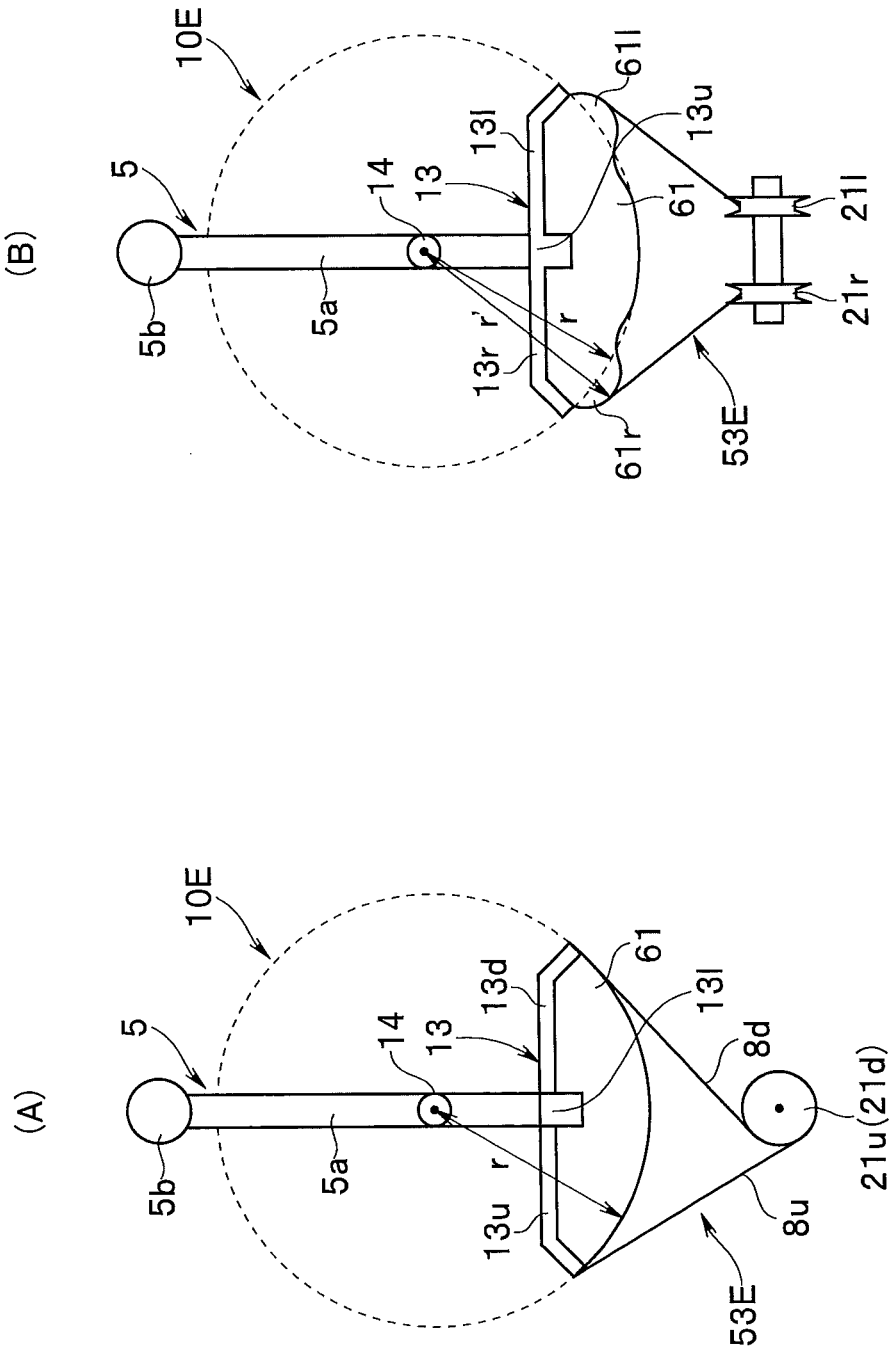
FIG. 15 is a side view showing a configuration near a manipulator in a second embodiment of the present invention.

In the present embodiment, a wire guide 61 shown in FIG. 15 is provided instead of the four wire guides 15i in the first embodiment to form an operation force amount adjusting portion 53E functioning as a direction adjusting member set (adjusted) to be capable of sensing a magnitude of an operation force amount in the up-down direction and the left-right direction.

In the first embodiment, the wire guides 15i are respectively provided in the portions of the four hanging arms 13i. However, in the present embodiment, the integral wire guide 61 is attached to the bottom surface of the hanging arm 13.

With respect to the up-down direction, the wire guide 61 is convex in the downward direction of the shaft portion 5a as shown in FIG. 15(A) and is formed in a curved surface shape formed along a fixed distance r from a rotation center of a bearing in the shaft portion 5a.

On the other hand, with respect to the left-right direction, the wire guide 61 is convex in the downward direction of the shaft portion 5a as shown in FIG. 15(B) but, near an end portion of the hanging arm 13, is formed in a curved surface shape including projecting surfaces 61l and 61r projecting to an outer side at the distance r (e.g., the projecting surface 61r has the distance r').

Note that curved surface shape portions shown in FIGS. 15(A) and 15(B) are respectively acting positions of a contact portion with which the hand side end portions of the bending wires 8i come into contact. An operation force amount is determined according to the acting positions of the contact portion.

Portions of the projecting surfaces 61l and 61r have a shape close to the shape of the projecting surface of the wire guides 15l and 15r in the first embodiment. A function of the portions is similar to the functions of the projecting surfaces in the first embodiment. However, when tilted a predetermined angle, a curved surface between the projecting surfaces 61l and 61r (i.e., a curved surface equivalent to the curved surface in the case of the up-down direction) functions as an acting position of the contact portion.

Therefore, a distribution of an operation force amount obtained when tilting operation is performed in the left-right direction and the up-down direction in the present embodiment has a characteristic like a characteristic chart shown in FIG. 16(A). In a relatively narrow bending range Wa as shown in FIG. 16(A), an operation force amount in the left-right direction is larger than an operation force amount in the up-down direction. Therefore, the operator can distinguish (sense), from a difference between the operation force amounts, with operation by a finger, for bending operation in which bending direction of the left-right direction and the up-down direction the tilting operation is performed.

Note that, for example, by further narrowing the shape of the projecting surfaces 61l and 61r, it is also possible to obtain a different characteristic in a narrower bending range Wb like a characteristic chart shown in FIG. 16(B). Further, by further expanding the shape of the projecting surfaces 61l and 61r, it is also possible to vary a characteristic in a wider bending range.

In the present embodiment, as shown in FIG. 15, a shape of the acting position of the contact portion with which the hand side end portions of the bending wires 8i of the wire guide 61 come into contact is formed to be different in the up-down direction and the left-right direction. Therefore, the operator can easily distinguish or sense, with a finger used for operation, in which direction of the up-down direction and the left-right direction bending operation is performed. Besides, as in the first embodiment, it is also possible to adjust a magnitude of an operation force amount with the wire guide 61.

Therefore, according to the present embodiment, by giving a difference to magnitudes of operation force amounts in performing bending operation in the up-down direction and the left-right direction, it is possible to sense an operation direction with a finger used for operation and it is possible to adjust a magnitude of an operation force amount. Note that a characteristic obtained by interchanging the characteristic shown in FIG. 16 in the up-down direction and the left-right direction may be set. In other words, a structure may be adopted in which the projecting surfaces 61l and 61r shown in FIG. 15(B) are provided on the wire guide 61 side shown in FIG. 15(A) and the projecting surfaces 61*l* and 61*r* are not provided on the wire guide 61 side shown in FIG. 15(B).

Figure 17:
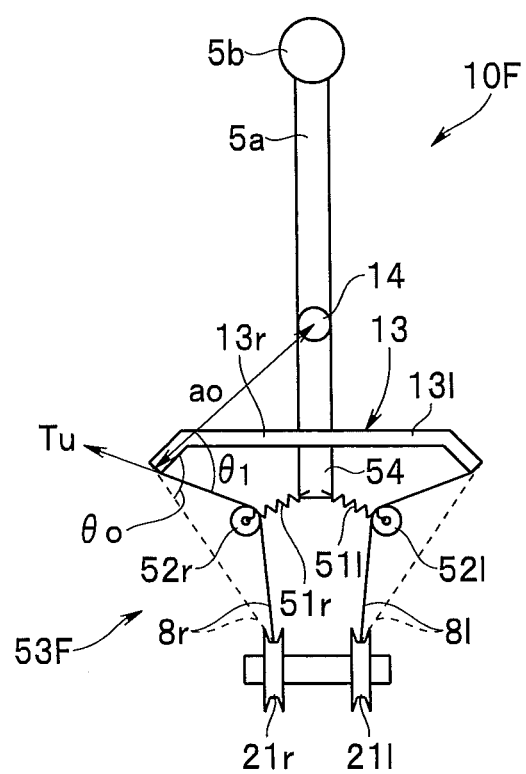
FIG. 17 is a diagram showing a schematic configuration of an operation input portion configured to perform tilting operation in a left-right direction in a modification of the second embodiment.

As a modification of the second embodiment, an input operation portion 1 OF that makes it easy to sense operation force amounts in the up-down direction and the left-right direction may be formed by applying a configuration close to the second modification of the first embodiment (the structure in which the springs 51*i* are used shown in FIG. 11) as shown in FIG. 17 referred to below.

In the modification shown in FIG. 17, a direction different from a direction (a direction close to horizontal in FIG. 11) in which the traction force amount Tu acts in the up-down direction shown in FIG. 11 is set by the springs 51*l* and 51*r*. An angle (or a supplementary angle) formed by a direction of the distance a and a direction in which the traction force amount Tu acts is indicated by θ1. Specifically, in FIG. 11, the angle θ formed by the direction extending from the center of the universal joint 14 to the wire fixing portion 13*u*2 and the direction of the traction force amount Tu is set. In this modification, the angle θ1 larger than the angle θ is set. That is, θ<θ1, where θ1<θ$_0$ and sin θ1<sin θ$_0$.

In this way, a direction of a traction force amount acting on the hand side end portions of the bending wires 8*i* is changed by an elastic force of the springs 51*i* to form an operation force amount adjusting portion 53F configured to adjust an operation force amount in operating the manipulator 5. A distribution of an operation force amount in the case of FIG. 17 is substantially the same as the characteristic chart of FIG. 16.

By using the springs 51*i* having different elastic forces are used in the up-down direction and the left-right direction, when tilting operation for bending in the up-down direction and the left-right direction is performed, operation force amounts are different. Therefore, the operator can easily distinguish a tilting direction from a difference in a magnitude of an operation force amount.

Note that, in the above explanation, when the tilting operation in the up-down direction or the left-right direction is further performed, operation force amounts may be set to be different. When the operation force amounts are set in that way, when the tilting operation in the up-down direction or the left-right direction is performed, it is also possible to grasp a tilting direction from a difference in a magnitude of an operation force amount.

Embodiments configured by, for example, partially combining the embodiments and the like explained above also belong to the present invention. Note that, in the present invention, contents of appended respective claims are substantially disclosed from described contents of the specification and the drawings.

What is claimed is:

1. An endoscope comprising:
   an insertion portion;
   a bending portion provided in the insertion portion and bendable in an up-down direction and a left-right direction;
   a traction member for bending the bending portion;
   an operation portion provided at a proximal end of the insertion portion and for grasping by an operator;
   an operation input portion provided in the operation portion, tiltable with respect to a direction for bending the bending portion in the up-down direction and a direction for bending the bending portion in the left-right direction, and for performing an operation input for acting on the traction member according to tilting operation and bending the bending portion; and
   an operation force amount adjusting portion configured to adjust an operation force amount for tilting the operation input portion in the direction for bending the bending portion in the up-down direction and an operation force amount for tilting the operation input portion in the direction for bending the bending portion in the left-right direction to be different, wherein
   the traction member includes an up-down direction traction member connected to the up-down direction side of the bending portion and inserted through the insertion portion and a left-right direction traction member connected to the left-right direction side of the bending portion and inserted through the insertion portion,
   the operation input portion includes a coupling member coupled to the up-down direction traction member and the left-right direction traction member and configured to tow the up-down direction traction member and the left-right direction traction member,
   the operation input portion has a pivoting axis and rotates around the pivoting axis,
   the coupling member includes a cross-shaped arm corresponding to the up-down direction and the left-right direction, a hand side end portion of the traction member being fixed to the arm, and
   the operation force amount adjusting portion is provided in the operation input portion, includes a contact portion configured to come into contact with the traction member extending from the coupling member and transmit an operation force amount due to titling of the operation input portion to the traction member, and enables an attachment position of the coupling member in a longitudinal direction of the arm to be changed so as to change a distance from the pivoting axis at the time when the traction member comes into contact with the contact portion near the coupling member and enable the operation force amount to be adjusted.

2. The endoscope according to claim 1, wherein the operation force amount adjusting portion further includes a resistor functioning as resistance in movement in a moving direction of the up-down direction traction member and the left and right direction traction member.

3. The endoscope according to claim 1, wherein
   the coupling member includes a cross-shaped arm extended from a proximal end in the operation input portion having a bar shape in a direction orthogonal to a longitudinal direction of the operation input portion and including an up-down direction arm to which respective hand side end portions of the up-down direction traction member are fixed and a left-right direction arm to which respective hand side end portions of the left-right direction traction member are fixed, and
   the operation force amount adjusting portion includes a first curved surface shape by an outer surface of an up-down direction traction member guide forming the contact portion, with which vicinities of hand side end portions of the up-down direction traction member provided at both ends in a longitudinal direction of the up-down direction arm come into contact, and a second curved surface shape by an outer surface of a left-right direction traction member guide forming the contact portion, with which vicinities of hand side ends of the left-right direction traction member provided at both ends in a longitudinal direction of the left-right direction arm come into contact, and respective portions in the first curved surface shape and the second curved surface shape are formed such that distances from the pivoting axis are different.

4. The endoscope according to claim 1, further comprising:
a C-ring shaped rotating body around which a wire configuring the traction member inserted through the insertion portion is wound, the rotating body being arranged to be loosely fit to an outer circumference of a pulley rotatable in the operation portion; and
a motor configured to rotate the pulley, wherein
the rotating body reduced in diameter according to a traction force acting on the wire comes into contact with an outer circumferential surface of the pulley in a rotating state such that a friction force is caused to act on the outer circumferential surface by the motor and tows, via the rotating body on which a rotating force acts in a rotating direction of the pulley, the wire wound around the rotating body in a direction in which the traction force acts.

5. An endoscope comprising:
an insertion portion;
a bending portion provided in the insertion portion and bendable in an up-down direction and a left-right direction;
a traction member for bending the bending portion;
an operation portion provided at a proximal end of the insertion portion and for grasping by an operator;
an operation input portion provided in the operation portion, tiltable with respect to a direction for bending the bending portion in the up-down direction and a direction for bending the bending portion in the left-right direction, and for performing an operation input for acting on the traction member according to tilting operation and bending the bending portion; and
an operation force amount adjusting portion configured to adjust an operation force amount for tilting the operation input portion in the direction for bending the bending portion in the up-down direction and an operation force amount for tilting the operation input portion in the direction for bending the bending portion in the left-right direction to be different, wherein
the operation force amount adjusting portion is provided in the operation input portion, includes a contact portion configured to come into contact with the traction member extending from the coupling member and transmit an operation force amount due to tilting of the operation input portion to the traction member, and changes a first distance between a position to which the traction member in the coupling member is coupled simultaneously with the tilting of the operation input portion and the pivoting axis to a second distance between an acting position where a traction force acts on the traction member in the contact portion and the pivoting axis so as to adjust an operation force amount necessary for the tilting of the operation input portion.

6. The endoscope according to claim 5, wherein
the traction member includes an up-down direction traction member configured to bend the bending portion in the up-down direction and a left-right direction traction member configured to bend the bending portion in the left-right direction, and
the operation force amount adjusting portion is provided in the coupling member to which at least one of the up-down direction traction member and the left-right direction traction member is coupled and adjusts the first distance to be larger than the second distance.

7. The endoscope according to claim 5, wherein
the traction member includes an up-down direction traction member configured to bend the bending portion in the up-down direction and a left-right direction traction member configured to bend the bending portion in the left-right direction,
the operation input portion has tilting directions in the up-down direction and the left-right direction respectively corresponding to the bending in the up-down direction and the bending in the left-right direction, and
the operation force amount adjusting portion is provided in the coupling member to which at least one of the up-down direction traction member and the left-right direction traction member is coupled and adjusts the first distance to be smaller than the second distance.

8. An endoscope comprising:
an insertion portion;
a bending portion provided in the insertion portion and bendable in an up-down direction and a left-right direction;
a traction member for bending the bending portion;
an operation portion provided at a proximal end of the insertion portion and for grasping by an operator;
an operation input portion provided in the operation portion, tiltable with respect to a direction for bending the bending portion in the up-down direction and a direction for bending the bending portion in the left-right direction, and for performing an operation input for acting on the traction member according to tilting operation and bending the bending portion; and
an operation force amount adjusting portion configured to adjust an operation force amount for tilting the operation input portion in the direction for bending the bending portion in the up-down direction and an operation force amount for tilting the operation input portion in the direction for bending the bending portion in the left-right direction to be different, wherein
the operation force amount adjusting portion further includes a guide roller, to which the other end of an elastic body having elasticity, one end of which is fixed to the operation input portion, for movably holding the traction member and urging the traction member in a held position to be towed to the one end side by the elastic body, changes a direction of the traction force acting on a hand side end portion of the traction member simultaneously with the tilting of the operation input portion to adjust the operation force amount necessary for the tilting of the operation input portion.

9. An endoscope comprising:
an insertion portion;
a bending portion provided in the insertion portion and bendable in an up-down direction and a left-right direction;
a traction member for bending the bending portion;
an operation portion provided at a proximal end of the insertion portion and for grasping by an operator;
an operation input portion provided in the operation portion, tiltable with respect to a direction for bending the bending portion in the up-down direction and a direction for bending the bending portion in the left-right direction, and for performing an operation input for acting on the traction member according to tilting operation and bending the bending portion; and
an operation force amount adjusting portion configured to adjust an operation force amount for tilting the operation input portion in the direction for bending the bending portion in the up-down direction and an operation force amount for tilting the operation input portion in the direction for bending the bending portion in the left-right direction to be different, wherein the traction member includes an up-down direction traction member configured to bend the bending portion in the up-down direction and a left-right direction traction member configured to bend the bending portion in the left-right direction, and the operation force amount adjusting portion further includes a plurality of guide rollers, to which the other ends of a plurality of elastic bodies having elasticity one ends of which are respectively fixed to the operation input portion, for movably holding the up-down direction traction member and the left-right direction traction member and urging the up-down direction traction member and the left-right direction traction member in held positions to be towed to the one ends side by the plurality of elastic bodies, and changes a direction of the traction force acting on respective hand side end portions of the up-down direction traction member and the left-right direction traction member simultaneously with the tilting of the operation input portion to adjust the operation force amount necessary for the tilting of the operation input portion in the up-down direction and the left-right direction.

10. The endoscope according to claim 9, wherein the coupling member further includes a cross-shaped arm extended from a vicinity of a proximal end in the operation input portion having a bar shape in a direction orthogonal to a longitudinal direction of the operation input portion and including an up-down direction arm to respective arm end portions of which respective hand side end portions of the up-down direction traction member are fixed and a left-right direction arm to respective arm end portions of which respective hand side end portions of the left-right direction traction member are fixed, and the guide roller includes four guide rollers configured to movably hold the up-down direction traction member and the left-right direction traction member respectively extended from the respective arm end portions.

\* \* \* \* \*